US009943599B2

(12) United States Patent
Gehl et al.

(10) Patent No.: US 9,943,599 B2
(45) Date of Patent: Apr. 17, 2018

(54) THERAPEUTIC APPLICATIONS OF CALCIUM ELECTROPORATION TO EFFECTIVELY INDUCE TUMOR NECROSIS

(71) Applicants: Herlev Hospital, Herlev (DK); Aarhus Universitet, Aarhus C (DK)

(72) Inventors: Karen Julie Gehl, Vanløse (DK); Stine Krog Frandsen, Frederiksberg C (DK); Jens Ole Eriksen, Værløse (DK); Hanne Margrethe Gissel Hyldkrog, Trige (DK); Pernille Højman Jensen, København S (DK)

(73) Assignee: HERLEV HOSPITAL, Herlev (DK)

( * ) Notice: Subject to any disclaimer, the term of this patent is extended or adjusted under 35 U.S.C. 154(b) by 291 days.

(21) Appl. No.: 14/367,439

(22) PCT Filed: Dec. 21, 2012

(86) PCT No.: PCT/DK2012/050496
§ 371 (c)(1),
(2) Date: Jun. 20, 2014

(87) PCT Pub. No.: WO2013/091657
PCT Pub. Date: Jun. 27, 2013

(65) Prior Publication Data
US 2015/0065946 A1    Mar. 5, 2015

Related U.S. Application Data

(60) Provisional application No. 61/579,175, filed on Dec. 22, 2011.

(30) Foreign Application Priority Data

Dec. 22, 2011 (EP) .................................. 11195435

(51) Int. Cl.
*A61B 17/20* (2006.01)
*A61K 41/00* (2006.01)
(Continued)

(52) U.S. Cl.
CPC ...... *A61K 41/0047* (2013.01); *A61K 31/7064* (2013.01); *A61K 33/06* (2013.01);
(Continued)

(58) Field of Classification Search
CPC ............ A61K 41/0047; A61K 41/0033; A61K 31/7064; A61K 33/06; A61K 33/14;
(Continued)

(56) References Cited

U.S. PATENT DOCUMENTS

2002/0061300 A1* 5/2002 Gokcen ................ A61K 38/164
424/94.2
2009/0081122 A1* 3/2009 Rufenacht .......... A61K 41/0052
424/1.29

FOREIGN PATENT DOCUMENTS

WO    WO 2007/144004 A1    12/2007

OTHER PUBLICATIONS

Winslow, Terese. "Tumor Size—Centimeters". Aug. 29, 2008. National Cancer Institute. https://visualsonline.cancer.gov/details.cfm?imageid=7200.*
(Continued)

*Primary Examiner* — Kevin C Sirmons
*Assistant Examiner* — Leah Swanson
(74) *Attorney, Agent, or Firm* — Knobbe, Martens, Olson & Bear, LLP

(57) ABSTRACT

The present inventors have shown that electroporation with calcium ions are efficient on cutaneous and subcutaneous nodules. In particular the present inventors here disclose that a solution comprising calcium ions ($Ca^{2+}$) with a concentration of at least 0.1 M is extremely useful in a method of
(Continued)

Figure 1:
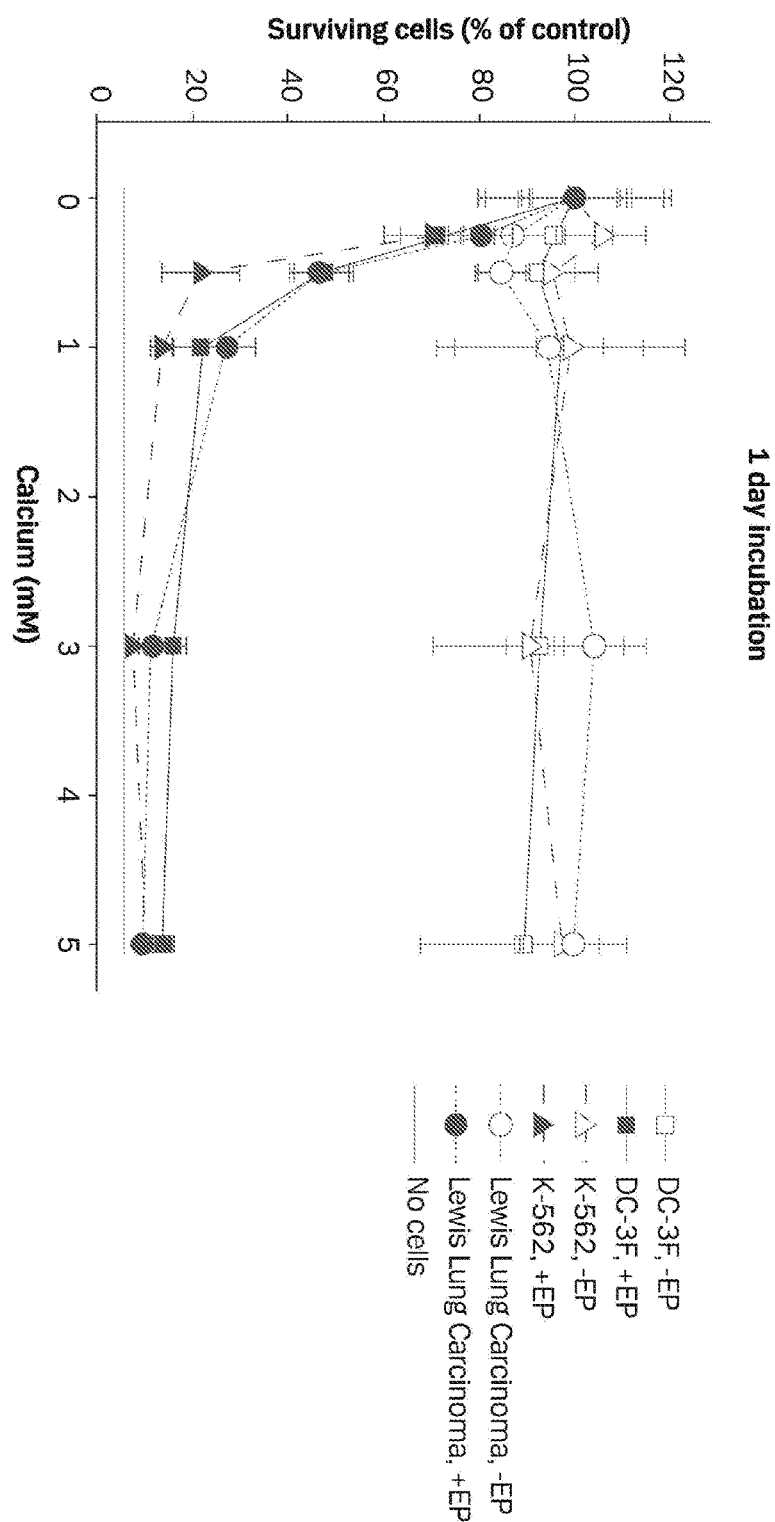

treating a neoplasm, such as cancer with means for causing transient permeabilization of the cell membranes of at least part of the neoplasm before, during and/or after administration of said solution, wherein said solution is administered with a ratio of 0.2 to 0.8 of the volume of said part of the neoplasm.

12 Claims, 18 Drawing Sheets

(51) Int. Cl.
```
A61K 33/14      (2006.01)
A61K 45/06      (2006.01)
A61K 38/14      (2006.01)
A61K 33/06      (2006.01)
A61K 31/7064    (2006.01)
A61M 5/14       (2006.01)
A61M 37/00      (2006.01)
A61N 1/32       (2006.01)
```
(52) U.S. Cl.
CPC .............. *A61K 33/14* (2013.01); *A61K 38/14* (2013.01); *A61K 41/0033* (2013.01); *A61K 45/06* (2013.01); *A61M 5/14* (2013.01); *A61M 37/0092* (2013.01); *A61N 1/327* (2013.01); A61M 2037/0007 (2013.01); A61M 2202/049 (2013.01); A61M 2250/00 (2013.01)

(58) Field of Classification Search
CPC ......... A61K 38/14; A61K 45/06; A61M 5/14; A61M 37/0092; A61M 2037/0007; A61M 2202/049; A61M 2250/00; A61N 1/327
USPC .......................................................... 604/22
See application file for complete search history.

(56) References Cited

OTHER PUBLICATIONS

Bonamassa, Barbara et al., "Hydrodynamic Gene Delivery and Its Applications in Pharmaceutical Research" Pharm Res, 2011, pp. 694-701, vol. 28.

Chen, C. et al., "Electroporation of cells using EM induction of ac fields by a magnetic stimulator" Physics in Medicine and Biology, 2010, pp. 1219-1229, vol. 55.

Clark, Paul R. et. al., "The inducible Hsp70 as a marker of tumor immunogenicity" Cell Stress & Chaperones, 2001, pp. 121-125, vol. 6, No. 2.

Frandsen, Stine Krog "Cytotoxic effect of calcium in supraphysiologic doses, internalized by electroporation" Master's thesis in Human Biology, Dec. 2010, Faculty of Health Science, Copenhagen University Department of Oncology, Copenhagen University Hospital Herlev.

Gissel, Hanne "Effects of varying pulse parameters on ion homeostasis, cellular integrity, and force following electroporation of rat muscle in vivo" Am J Physiol Regul Integr Comp Physiol, Jan. 27, 2010, pp. R918-R929, vol. 298.

Golzio, Par M. et al., "Calcium et cellules electropermeabilisees" Journal de la Societe de Biologie, 2003, pp. 301-310, vol. 197, No. 3—Abstract.

Hojman, Pernille et al., "Calcium Electrotransfer for Termination of Transgene Expression in Muscle" Human Gene Therapy, Jun. 2011, pp. 753-760, vol. 22.

Kircheis, R. et al., "Tumor-targeted gene delivery: an attractive strategy to use highly active effector molecules in cancer treatment" Gene Therapy, 2002, pp. 731-735, vol. 9.

Kusmartsev, Sergei et al., "All-trans-Retinoic Acid Eliminates Immature Myeloid Cells from Tumor-bearing Mice and Improves the Effect of Vaccination" Cancer Research, Aug. 1, 2003, pp. 4441-4449, vol. 63.

Kusmartsev, Sergei et al., "Tumor-Associated $CD8^+$ T Cell Tolerance Induced by Bone Marrow-Derived Immature Myeloid Cells" The Journal of Immunology, 2005, pp. 4583-4592, vol. 175.

Lee, Raphael C. "Cell Injury by Electric Forces" Ann. N.Y. Acad. Sci., 2005, pp. 85-91, vol. 1066.

Liu, Jin et al., "Non-Invasive Assessment and Control of Ultrasound-Mediated Membrane Permeabilization" Pharmaceutical Research, 1998, pp. 918-924, vol. 15, No. 6.

Ma, Hak-Ling et al., "IL-21 Activates both innate and adaptive immunity of generate potent antitumor responses that require perforin but are independent of IFN-γ" The Journal of Immunology, 2003, pp. 608-615, vol. 171.

Mashiba, H. et al., "Device for intracellular increase of oxygen free radicals and inhibition of MethA tumour cell proliferation: in vitro and in vivo studies" Int. J. Tiss. Reac., 1988, pp. 273-280, vol. X, No. 5.

Mashiba, et al., "Proliferation inhibition of human cancer cells by intracellular introduction of calcium chloride in combined use with electroporation" American Association for Cancer Research. Proceedings of the Annual Meeting, Mar. 2001, p. 377, vol. 42, XP-001536403.

Mashiba, H. et al., "Augmented antiproliferative and antitumor effect on methA tumor cells in combined use of electroporation with calcium chloride" International Journal of Cancer, Supplement, Jan. 2002, p. 433, No. 13, XP-001536405.

Mashiba, H. et al., "Augmentation of antitumor and antimetastatic effect in combined use of electroporation with calcium chloride" American Association for Cancer Research, Proceeding of Annual Meeting, Apr. 2005, pp. 528-529, vol. 46, Suppl S, 20, XP-001536404.

Rakhmilevich, Alexander L. et al., "Gene gun-mediated skin transfection with interleukin 12 gene results in regression of established primary and metastatic murine tumors" Proc. Natl. Acad. Sci., Jun. 1996, pp. 6291-6296, vol. 93.

Stelljes, Matthias et al., "Differential Requirement for a Cellular Type-1 Immune Response in Tumor-Associated Versus Alloantigen-Targeted GvT Effects" Transplantation, Feb. 15, 2007, pp. 314-322, vol. 83, No. 3.

Tang, Li-Ling et al., "Steep pulsed electric fields modulate cell apoptosis through the change of intracellular calcium concentration" Colloids and Surfaces B: Biointerfaces, 2007, pp. 209-214, vol. 57.

Teruel, Mary N. et al., "Electroporation-induce formation of individual calcium entry sites in the cell body processes of adherent cells" Biophysical Journal, Oct. 1997, pp. 1785-1796, vol. 73.

Yang, W. et al., "Differential Sensitivities of Malignant and Normal Skin Cells to Nanosecond Pulsed Electric Fields" Technology in Cancer Research and Treatment, Jun. 2011, pp. 281-286, vol. 10, No. 3.

* cited by examiner

2 hours after CaCl$_2$ + EP

HE, original magnification 20x

HE, original magnification 400x

6 days after CaCl$_2$ + EP

HE, original magnification 20x

HE, original magnification 400x

A – LPB (murine sarcoma) tumors

B – B16 (murine melanoma) tumors

A – MDA_MB231 (human breast cancer) tumor

B – HT29 (human colon cancer) tumor

C – SW780 (human bladder cancer) tumor

Before treatment     1 day after treatment     11 days after treatment

A

B

A

B

THERAPEUTIC APPLICATIONS OF CALCIUM ELECTROPORATION TO EFFECTIVELY INDUCE TUMOR NECROSIS

CROSS REFERENCE TO RELATED APPLICATIONS

This application is a U.S. National Phase application of PCT International Application Number PCT/DK2012/050496, filed on Dec. 21, 2012, designating the United States of America and published in the English language, which is an International Application of and claims the benefit of priority to European Patent Application No. 11195435.0, filed on Dec. 22, 2011, and U.S. Provisional Application No. 61/579,175, filed on Dec. 22, 2011. The disclosures of the above-referenced applications are hereby expressly incorporated by reference in their entireties.

FIELD OF THE INVENTION

The present invention relates to calcium overloading by transient permeabilisation of cell membranes leading to ATP depletion and cell necrosis of neoplasms, which is useful in the treatment of cancer. In particular, the present invention relates to electroporation with calcium for the removal of malignant tissue.

BACKGROUND OF THE INVENTION

Calcium is a ubiquitous second messenger involved in many cellular processes, including regulation of transcription, metabolism, proliferation, muscle contraction, and cell death both via apoptosis and necrosis.

Due to the many effects of calcium, the intracellular calcium concentration is tightly regulated, and the effects of calcium are dependent on time, place, amplitude, frequency, and duration of the calcium signal. Cellular uptake of calcium can be facilitated by electroporation, where cells are exposed to an electric field exceeding the dielectric strength of the cell membrane, resulting in generation of reversible permeabilisation structures in the membrane. This allows flux of normally non-permeating ions and molecules across the membrane.

In eukaryotic cells the concentration of free intracellular calcium is very low ($10^{-7}$M), in striking contrast to the concentration of free calcium in plasma ($10^{-3}$M). Thus, even a small increase in the permeability of the membrane may increase the concentration of free intracellular calcium drastically. Increase in intracellular calcium concentration due to electroporation has previously been shown, but its use in cancer treatment has not been fully investigated.

Electroporation has been used for local treatment of malignant tumors in combination with chemotherapeutic agents (electrochemotherapy) or plasmids (gene electrotransfer) in clinical trials. The cytotoxic agents bleomycin or cisplatin have been used, either by intravenous or intratumoral route, followed by application of electric pulses to the tumor. Standard operating procedures of electrochemotherapy using chemotherapeutics have been known for a few years, best illustrated by Mir et al. [2006].

Mashiba et al [2005] discloses a repetitive combination therapy that use 2% calcium chloride in combination with electroporation to induce apoptosis in human cancer cells. Intralesional injection of calcium chloride (2%, 0.1 ml) and subsequent electroporation of mice bearing the methA murine tumor cell is also disclosed. Mashiba et al [2005] is silent about any required treatment regime to the dosage of the volume required in order to avoid side effects in the surrounding tissues and particularly it is not clear from Mashiba et al [2005] what the volume of the tumors is.

Hence, an improved method for treating cancer would be advantageous, in particular a more efficient method with less side effects would be preferable.

SUMMARY OF THE INVENTION

Here we document that calcium electroporation can be highly efficient in eradicating tumors in vivo. The mechanistic explanation is acute energy depletion leading to necrosis.

Thus, an object of the present invention relates to a method for treating a neoplasm comprising
 a) providing a subject having at least one neoplasm;
 b) administering to said subject a solution comprising calcium ions ($Ca^{2+}$) with a concentration of at least 0.1 M to at least a part of said neoplasm, wherein the volume of the solution has a ratio of 0.2 to 0.8 of the volume of said part of the neoplasm; and
 c) applying means for causing transient permeabilisation of the cell membranes in said part of the neoplasm before and/or during and/or after said administration.

In particular, it may be seen as an object of the present invention to provide a solution comprising calcium ions ($Ca^{++}$) with a concentration of at least 0.1 M is extremely useful in a method of treating a neoplasm, such as cancer with means for causing transient permeabilisation of the cell membranes of at least part of the neoplasm before, during and/or after administration of said solution, wherein said solution is administered with a ratio of 0.2 to 0.8 of the volume of said part of the neoplasm that e.g. solves the lack of a fully effective and yet safe handling regime for treating cancer.

In the following the present invention will be described in detail.

DETAILED DESCRIPTION OF THE INVENTION

The aim of the present invention is to define a standard operating procedure (SOP) to safely and conveniently treat patients with neoplasms with a drug that is extremely simple and efficient. The present invention differs from the art in that highly efficient tumor cell kill may be obtained without the use of a chemotherapeutic agent, using calcium and electroporation alone. The surrounding cells are relatively spared during the treatment regime disclosed which is a known side effects in the art with other drugs used in combination with electroporation. The tumors tested by the present inventors show continuous regression with necrosis being induced instead of apoptosis. Necrosis is known to be far more effective mechanism for successful removal of tumors, as tumors often are relatively resistant to apoptosis.

The present inventors have shown that electroporation with calcium ions is efficient on cutaneous and subcutaneous nodules. In particular, the present inventors here disclose, that a solution comprising calcium ions ($Ca^{++}$) with a concentration of at least 0.1 M is extremely useful in a method of treating a neoplasm, such as cancer with means for causing transient permeabilisation of the cell membranes of at least part of the neoplasm before, during and/or after administration of said solution, wherein said solution is administered with a ratio of 0.2 to 0.8 of the volume of said part of the neoplasm.

Thus, in one aspect the present invention relates to a method for treating a neoplasm comprising
  a) providing a subject having at least one neoplasm;
  b) administering to said subject a solution comprising calcium ions ($Ca^{++}$) with a concentration of at least 0.1 M to at least a part of said neoplasm, wherein the volume of the solution has a ratio of 0.2 to 0.8 of the volume of said part of the neoplasm; and
  c) applying means for causing transient permeabilisation of the cell membranes in said part of the neoplasm before, during or after said administration.

The present invention is a new neoplasm or tumor ablation modality providing delivery into cell interiors of non-permeant drugs with intracellular targets. It is based on the local application of e.g. short and intense electric pulses that transiently permeabilise cells in tissues or alternatively by sonoparation. Thus, in step b) the calcium solution is administered to the neoplasm and in step c) (without being bound by theory) the calcium is further administered intracellularly due to the transient cell permeabilisation thereby increasing the intracellular calcium level throughout the neoplasm. Thus, step b) and c) may both considered administration routes.

In an embodiment administration in step b) is performed by injection. In another embodiment intracellular administration in step c) is performed by electroporation, sonoporation, hydrodynamics-based procedures or magnetic fields as used in magnetic resonance technology (MR).

The inventors here disclose treatment of tumor nodules when the electric pulses are associated with calcium ions having a high intrinsic cytotoxicity and/or an effect leading to necrosis.

It is important to note that the physico-chemical basis of this treatment allow the method to be applied on all tumors types. Both the in vitro and in vivo results disclosed clearly support this assessment. It actually brings a complete new world of indications for calcium ions combined with transient permeabilisation, and the data disclosed demonstrated the effectiveness of this technique, which overcomes the side effects of classical chemotherapy, allows avoidance of surgery, or possibility of treatment when surgery is deemed impossible, for example in previously irradiated areas.

It has repeatedly been shown with electrochemotherapy using e.g. bleomycin that hemorrhagic nodules stop bleeding immediately after treatment, and the pain of painful lesions may also be reduced, thus such effects are also immediately applicable by the present invention.

The consequences of this treatment are simple, and taking into account the economic issues, the cost of this method is really low. This therapy should therefore be offered to patients to improve their quality of life independently of life expectancy, to heal painful and/or bleeding lesions, as well as to improve the patient's cosmesis and associated social interactions.

Though the data presented relates to tumors and the efficient anti-cancer treatment, the power of the present invention relates to all types of neoplastic cells a physician would consider treating.

A particular advantage of the present invention is that it may limit the amount of surgery or treatments necessary for treating cancer, it is envisaged that the present invention, due to its extremely high efficiency, will enable the skilled addressee to merely apply the present invention to a patient in need thereof—one or a few times in a single procedure—as compared to repetitive treatments observed with less efficient methods when dealing with complicated tumors and following relapses.

Thus, in another aspect the present invention can be defined as a solution comprising calcium ions ($Ca^{++}$) with a concentration of at least 0.1 M for use in a method of treating a neoplasm (or for use in the treatment of a neoplasm), said method comprising
  a) providing a subject having at least one neoplasm;
  b) administrating to said subject a solution comprising calcium ions ($Ca^{++}$) with a concentration of at least 0.1 M to at least a part of said neoplasm, wherein the volume of the solution has a ratio of 0.2 to 0.8 of the volume of said part of the neoplasm; and
  c) applying means for causing transient permeabilisation of the cell membranes in said part of the neoplasm before and/or during and/or after said administration.

Again, in step b) the calcium solution is administered to the neoplasm and in step c) (without being bound by theory) the calcium is further administered intracellularly due to the transient cell permeabilisation thereby increasing the intracellular calcium level through-out the neoplasm. Thus, step b) and c) may both considered administration routes.

The means for causing transient permeabilisation of the cell membranes are preferably done after administration of calcium to at least a part of said neoplasm.

It will be evident for the skilled addressee that the information presented in the present application combined with e.g. standard operating procedures of electrochemotherapy as disclosed by Mir et al., allows the physicians using the invention to select the type of anaesthesia and the means for causing transient permeabilisation. Thus, whether to apply this invention as a one time use for a particular patient for a single session or use repeatedly on e.g. large tissue neoplasms such as but not limited to large tumors or even treat several nodules of the same patient in a given session lies within the scope of the present invention.

Thus, in an embodiment step b) and/or step c) is repeated one or more times to improve the treatment, such as but not limited to 1-10 times, such as 1-5 times, such as 1-3 times regime. In an embodiment only step c) is repeated. In another embodiment step b) is repeated before step c) is initiated.

It may happen e.g. in the case of the treatment of a large number of nodules or of lesions of very different sizes, that more than one means for causing transient permeabilisation have to be used.

The present invention is also a novel method for lowering the probability of recurrence of tumor growth in otherwise normal tissues surrounding a site of excised cancerous cells. In other words, the invention method comprises treating "margins" of tissue surrounding a site of cancer cells, such cancerous cells typically formed at a distinct tissue site.

In a preferred embodiment, the invention method provides for reducing the amount of tissue that must be excised along with the tumor and its cancerous cells and making radiation or chemotherapy superfluous.

The method may comprise applying transient permeabilisation to the tissues surrounding the tumor site.

Alternatively, the method relates to reducing recurrence of neoplastic cell growth in a mammalian tissue comprising
  a) providing a source for applying a transient permeabilisation to said tissue;
  b) administering calcium ions to said tissue; and
  c) applying the transient permeabilisation to said tissue, thereby delivering said calcium ions into said cells resulting in reducing or eliminating neoplastic cell growth with necrotic effect.

In another aspect the present invention relates to a system for treating a mammal tissue comprising cells located adjacent to and/or near to a neoplastic site comprising:
  a) a transient permeabilisation device; and
  b) a therapeutic substance or solution comprising calcium ions according to the present invention.

In a further aspect the invention relates to a solution comprising a concentration of at least 0.1 M calcium ions for use in the ablation of malignant and non-malignant tissue structures,
  wherein the ratio between the volume of the composition and the volume of the tissue structure is in the range 0.2 to 0.8, and
  wherein the calcium solution is administered translesional to said tissue structures before, during and/or after transient permeabilisation to said tissue structures.

Treating a Neoplasm

A neoplasm is abnormal proliferation, thus when neoplasms become of importance in medical conditions, then the abnormal proliferation generates an unregulated cell growth forming e.g. tumors, and invade nearby parts of the body.

Thus, controlling or eradicating such a neoplastic tissue is increasingly a demand for treating, preventing or inhibiting these conditions. Typically, neoplasms have been treated with chemotherapeutic agents, surgery, radiotherapy and/or other antineoplastic drugs.

Neoplasm

In the present context the term neoplasm relates to abnormal proliferation of cells. A neoplasm can be benign, potentially malignant (pre-cancer), or malignant (cancer). Benign neoplasms include uterine fibroids and melanocytic nevi. They rarely transform into cancer. Potentially malignant neoplasms include carcinoma in situ. They do not invade and destroy but, given enough time, may progress to invasive cancer. Malignant neoplasms are commonly called cancer. They invade and destroy the surrounding tissue, may form metastases and eventually kill the host.

In a preferred embodiment the neoplasms of the present invention relates to an abnormal mass of tissue, the growth of which exceeds and is uncoordinated with that of the normal tissues, and persists in the same excessive manner after cessation of the stimulus which evoked the change.

It should be understood that any feature and/or embodiment discussed herein in connection with the neoplasm according to the invention apply by analogy to tumor and cancers, and these terms may be used interchangeably.

Tumor

Typically, the term tumor is used as a synonym of neoplasm. However, some neoplasms do not form a tumor. These include leukaemia and most forms of carcinoma in situ. Thus, there is a distinction between a solid or fluid-filled (cystic) lesion that may or may not be formed by an abnormal growth of neoplastic cells.

Tumor is not synonymous with cancer. While cancer is by definition malignant, a tumor can be benign, pre-malignant, or malignant, or can represent a lesion without any cancerous potential whatsoever.

In the present context a tumor is a lesion that is formed by an abnormal growth of neoplastic cells that appears enlarged in size.

Cancer

In the present context cancer is a malignant neoplasm, which is a large group of different diseases, all involving unregulated cell growth. In cancer, cells divide and grow uncontrollably, forming malignant tumors, and invade nearby parts of the body. The cancer may also spread to more distant parts of the body through the lymphatic system or bloodstream. Not all tumors are cancerous. Benign tumors do not grow uncontrollably, do not invade neighbouring tissues, and do not spread throughout the body.

In one embodiment the cancer is solid tumor cancer. In a preferred embodiment, the solid tumor cancer is selected from the group consisting of but not limited to Carcinoma, Sarcoma, Lymphoma, Germ cell tumor and Blastoma.

In yet another embodiment the solid tumor cancer is selected from the group consisting of Bladder Cancer, Lung Cancer, Breast Cancer, Melanoma, Colon and Rectal Cancer, Non-Hodgkin Lymphoma, Endometrial Cancer, Pancreatic Cancer, Kidney (Renal Cell) Cancer Prostate Cancer, Head and Neck Cance[r], Thyroid Cancer, non-melanoma skin cancer such as, but not limited to, basocellular carcinoma and brain cancer.

Not all cancers initially form tumors, but may be" free flowing" cells e.g. in the blood stream, lymphoid system or bone marrow. An example of such cancer type is leukemia. Thus, in an embodiment the cancer is leukemia. In a further embodiment the leukemia is selected from the group consisting of Acute lymphoblastic leukemia (ALL), Chronic lymphocytic leukemia (CLL), Acute myelogenous leukemia (AML), Chronic myelogenous leukemia (CML), Hairy cell leukemia (HCL), T-cell prolymphocytic leukemia (T-PLL), Large granular lymphocytic leukemia and Adult T-cell leukemia.

Cancers, such as leukemia, may also be treated by a method according to the present invention, wherein the treatment takes place ex vivo. For example a blood sample or purified blood sample may be exposed to transient cell permeabilisation ex vivo (in the presence of elevated calcium levels) and then be returned to the subject from which the sample was obtained.

Such cell permeabilisation may take place in a separate chamber. This type of treatment may be performed in a similar way as dialysis, wherein the dialysis apparatus comprises means for providing transient cell permeabilisation of the cells or a group of cells in the blood sample passing through the dialysis apparatus. In addition the apparatus may comprise means for providing an elevated concentration of calcium to the blood sample being treated. Preferably the increased calcium concentration is supplied to the blood stream upstream or simultaneously with the induction of cell permeabilisation.

As the skilled addressee would recognise then neoplasms of the present invention vary substantially in size from a few millimeters to several centimeters. The present inventors have clinically observed neoplasm such as chest wall recurrence of breast cancer that measured over 25 cm in diameter. At present typical means for causing transient permeabilisation of the cell membranes such as but not limited to electroporation uses electrodes that are only around a few centimeters, thus when the person skilled in the art wants to apply the present invention on larger neoplasm he would have to use several pulse applications to cover the neoplasm volume.

Since electrochemotherapy has proven efficient in cutaneous tumors, electrodes facilitating the application of electroporation for use in colorectal cancer, bone and liver metastases, and brain tumors have been developed, and are now in clinical trials, the present invention may be used to treat cancers, such as but not limited to, for example primary or metastatic tumors of any histology in the brain, head and neck area, lungs, liver, intestinal system, bones, and connective tissue.

Since the cell membrane is a common feature to all tumor cells, and since high intracellular calcium levels are toxic to all cells, this treatment is applicable to all cancer histologies, including, but not limited to, Malignant melanoma, adenocarcinoma from breast, colon, rectum, planocellular carcinoma from head and neck cancer, lung cancer, vulvar, uterine, cervical, and anal cancer.

The present invention is also applicable to malignant tumors arising from the skin, such as basocellular carcinoma, planocellular carcinoma or Merckel cell tumors. Sarcomas including kaposi's sarcoma renal cell carcinoma and transitocellular carcinoma of the bladder, thyroid cancer, hepatocellular carcinoma, glioblastoma and other neoplams of the brain.

The margin tissue surrounding tumors that is typically amenable to treatment include, without limitation, those of organs including breast, prostate, tongue, penis, labia, rectum, vocal chords, liver, connective and cutaneous tissues. The present invention can be performed on such tissues whether the tumor mass has been removed or not. In such cancers the patient would be helped substantially by treating the tissues in a manner wherein healing can proceed largely unimpaired and there is a possibility of eliminating microscopic metastases and tumor branches growing into the tissues that give rise to local recurrences. As is also understandable with respect to the invention provide for a measurable degree of selectivity in targeting cancerous cells, since the permeabilisation is required and differences in threshold for permeabilisation have been observed between normal and malignant cells.

Additionally, use of the invention is also applicable to disease states where sites of cancerous cells are distributed in areas not easily amenable to surgery. For example, skin tissues of the face containing microscopic or focal disease sites can be treated with the invention in the same manner as used for treating a margin tissue bed resulting in substantially less scarring than would be caused by surgery. Thus, the invention methods can be used as an adjuvant to surgery or even a neo-adjuvant.

In the examples of the present application, the inventors disclose direct use of intratumoral calcium injection followed by electroporation or sonoporation. Since calcium for injection is commercially available and regularly used at most hospitals and electric pulses are already used clinically, this treatment could easily be implemented into the clinic. In addition, calcium has an excellent safety profile both for use in patients and for staff, and would not need administration by staff accredited to administer chemotherapy. Finally, cost of cancer treatment is causing global concern, and calcium electroporation is both simple and inexpensive and is likely to be of potential benefit in the treatment of local tumors regardless of histology.

In one embodiment, the use of calcium ions as disclosed herein may be combined with other drugs, such as but not limited to chemotherapeutic drugs, such as but not limited to bleomycin and/or cisplatin for local treatment.

In another embodiment calcium electroporation may be used with other systemic chemotherapeutic agents, including but not limited to cyclophosphamide, taxanes, doxorubicin, other platinum compounds, to enhance a local response.

Though calcium may be used in combination with other chemotherapeutic drugs, this is not always desirable, since such drugs are often cell-toxic and therefore must be handled with care. Oppositely, calcium is non-toxic and can therefore be handled without special precautions, e.g. also by veterinarians. Thus, in an embodiment, the solution comprising calcium ions is substantially free or completely free from other cell-toxic components, such as other chemotherapeutic drugs such as but not limited to bleomycin and/or cisplatin.

In another embodiment, the present invention relates to a method of reducing the probability of recurrence of cancer cell growth in a tissue. Such methods includes providing to the cells of said tissue both an electroporating pulse of electric energy or other means for causing transient permeabilisation of the cell membranes and a medicament or solution of the present invention, and the medicament or solution is preferably provided to the tissue immediately prior to, simultaneously and/or immediately after the electroporating pulse.

In a further embodiment, the invention comprises a method of treating residual cancerous cells remaining in tissues following surgical resection. Preferably, the invention provides for controlling further spreading of cancer by subjecting microscopic nodules or other forms of cancerous tissue to the calcium ions in e.g. an electroporating electric field.

In a related embodiment, such treatment can be an adjuvant to surgery in that it can be applied either prior to or after tumor removal. In some circumstances, especially where the cancerous cells have not yet formed into a fibrous mass, no surgical procedure may be employed. In such case, the present invention provides a method to reduce tumor mass and terminate or delay further growth of cancerous cells in the tissue.

In still a further related embodiment, the invention methods provide for debulking of larger tumor masses by causing through the effect of an anticancer agent of the present invention, even in combination with other anticancer agents (e.g. chemotherapeutics), such as but not limited to bleomycin, a necrosis of the tumor tissue such that the tumor mass will be easier to remove from surrounding healthy or normal tissue. In the example section calcium is also tested in combination with bleomycin.

Subject Having at Least One Neoplasm

The criteria that must be checked during pre-inclusion visits for the treatment by the present invention will of course always determine whether the patient will benefit from this treatment. Due to the extremely simple and efficient effects disclose by the present invention, the inventors disclosed that after determination of neoplastic growth or cancer based on symptoms, medical history, risk factors, and clinical tests the use of calcium ions and transient permeabilisation of the cell membranes only should cause exclusion of patients or special attention should be paid when:

The presence of a pacemaker precludes treatment on e.g. the anterior chest wall

If the subject is taking anticoagulants, this should be paused

If any previous difficulties with local or general anaesthesia

In one embodiment the present invention relates to the treatment of subjects, wherein the subject is a mammal.

In the present context the term "a mammal" includes but is not limited to a human; a non-human species, including but not limited to a primate; a livestock animal such as a sheep, a cow, a pig, a horse, a donkey, or a goat; a laboratory test animals such as mice, rats, rabbits, guinea pigs, or hamsters; and a companion animal such as a dog or a cat.

Thus, in an embodiment the subject is a mammal such as but not limited to a human; a non-human species, including a primate; a livestock animal such as a sheep, a cows, a pig, a horse, a donkey, or a goat; a laboratory test animals such as mice, rats, rabbits, guinea pigs, or hamsters; or a companion animal such as a dog or a cat.

In a presently preferred embodiment the mammal is a human.

The Calcium Solution

The source of calcium ions ($Ca^{++}$) suitable for generating the required calcium overload of the present invention is typically originating from calcium chloride, calcium gluconate or calcium glubionate.

The skilled addressee would immediately recognise that the concentration of the calcium solution is variable, but from a practical view point should be at least 0.1 M, such as but not limited to at least 0.15 M, at least 0.2 M, at least 0.3 M, at least 0.4 M, at least 0.5 M, at least 0.6 M, at least 0.7 M, at least 0.8 M, at least 0.9 M, at least 1 M, or even higher concentrations can be used, as long as the calcium ions can be widely distributed in the neoplastic tissue. In another embodiment the calcium is present in a concentration in the range 0.1-2 M, such as but not limited to 0.1-1.5 M or such as in the range 0.1-1M.

It is to be understood that the calcium source is provided in a physiological acceptable carrier, e.g. water of a buffer system.

Several commercial available products exist as ready to use solutions, such as but not limited to CALCIUM-SANDOZ®, which is a 9 mg Ca/ml solution. The present inventor also used mixtures prepared by SAD (Denmark) with a 0.5 mmol/ml solution.

The Solution Volume Versus Tumor Volume Ratio

Shown herein is that injecting isotonic calcium-chloride corresponding to half the tumor volume followed by electroporation was highly efficient. Efforts are also being made to perform irreversible electroporation of tumors where addition of calcium could enhance efficacy, in particular because inhomogeneities in the electric field may cause part of the tumor to be only reversibly permeabilised. In this case, addition of calcium would enlarge the volume where efficient tumor cell kill is obtained.

Figure 6:
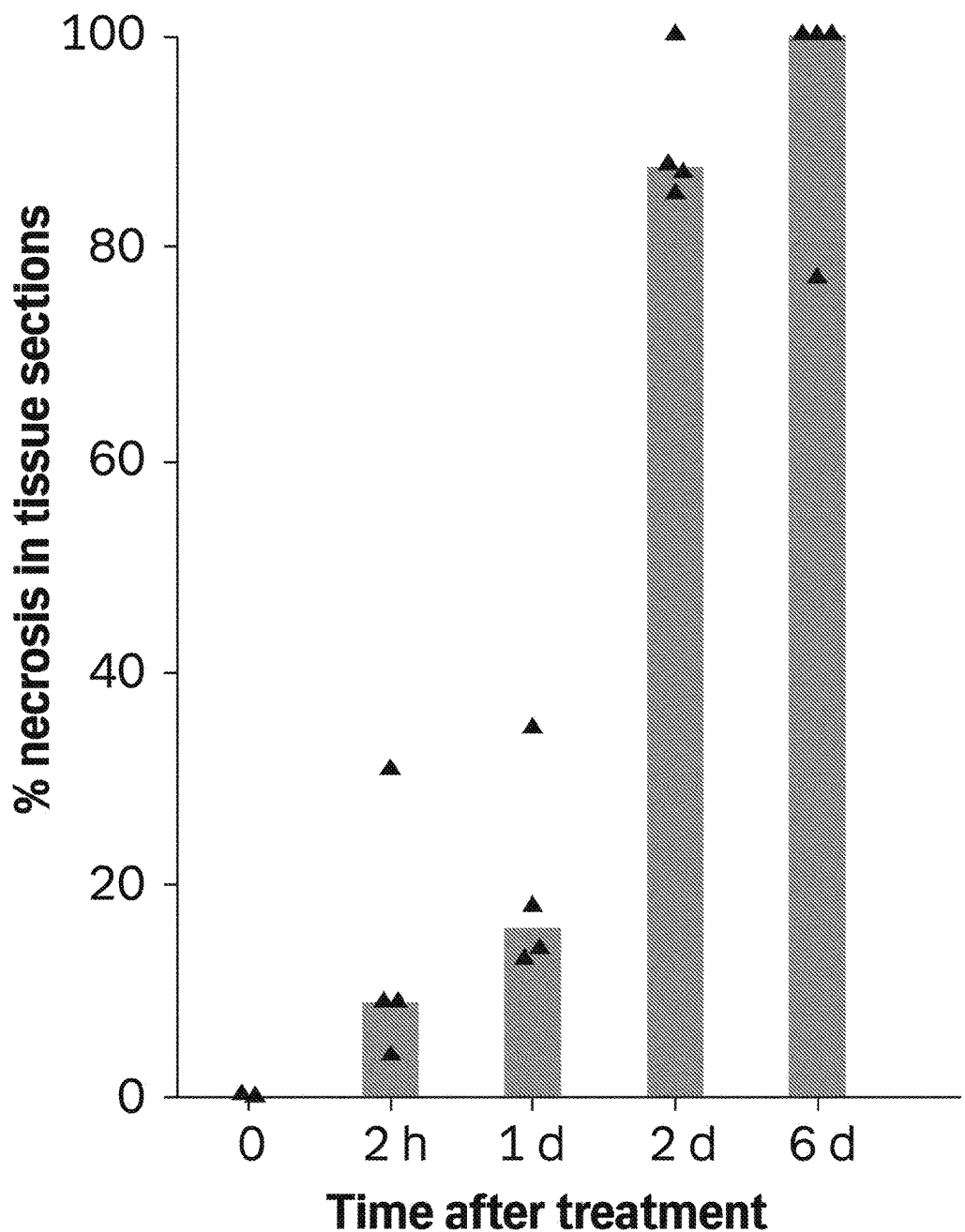
Figure 7:
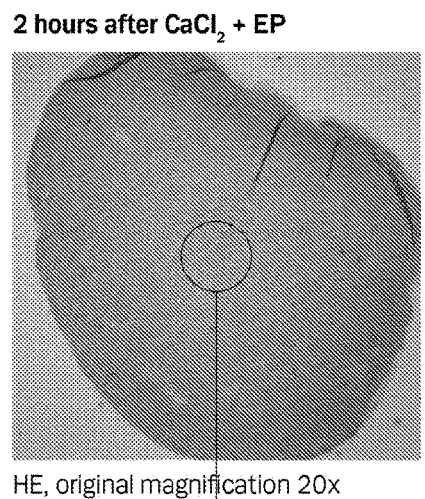
Figure 7:
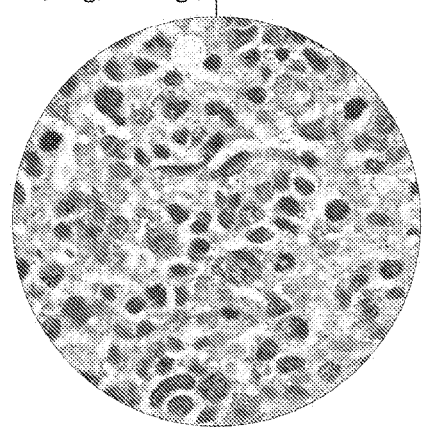
Figure 7:
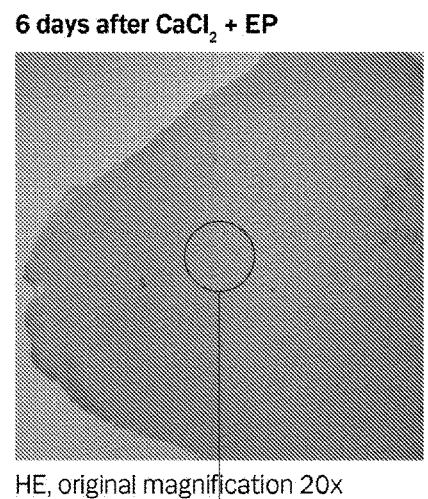
Figure 7:
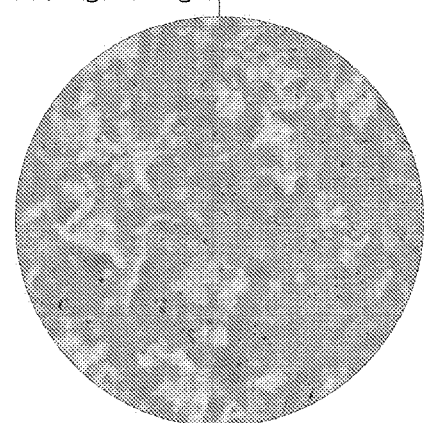
Figure 8:
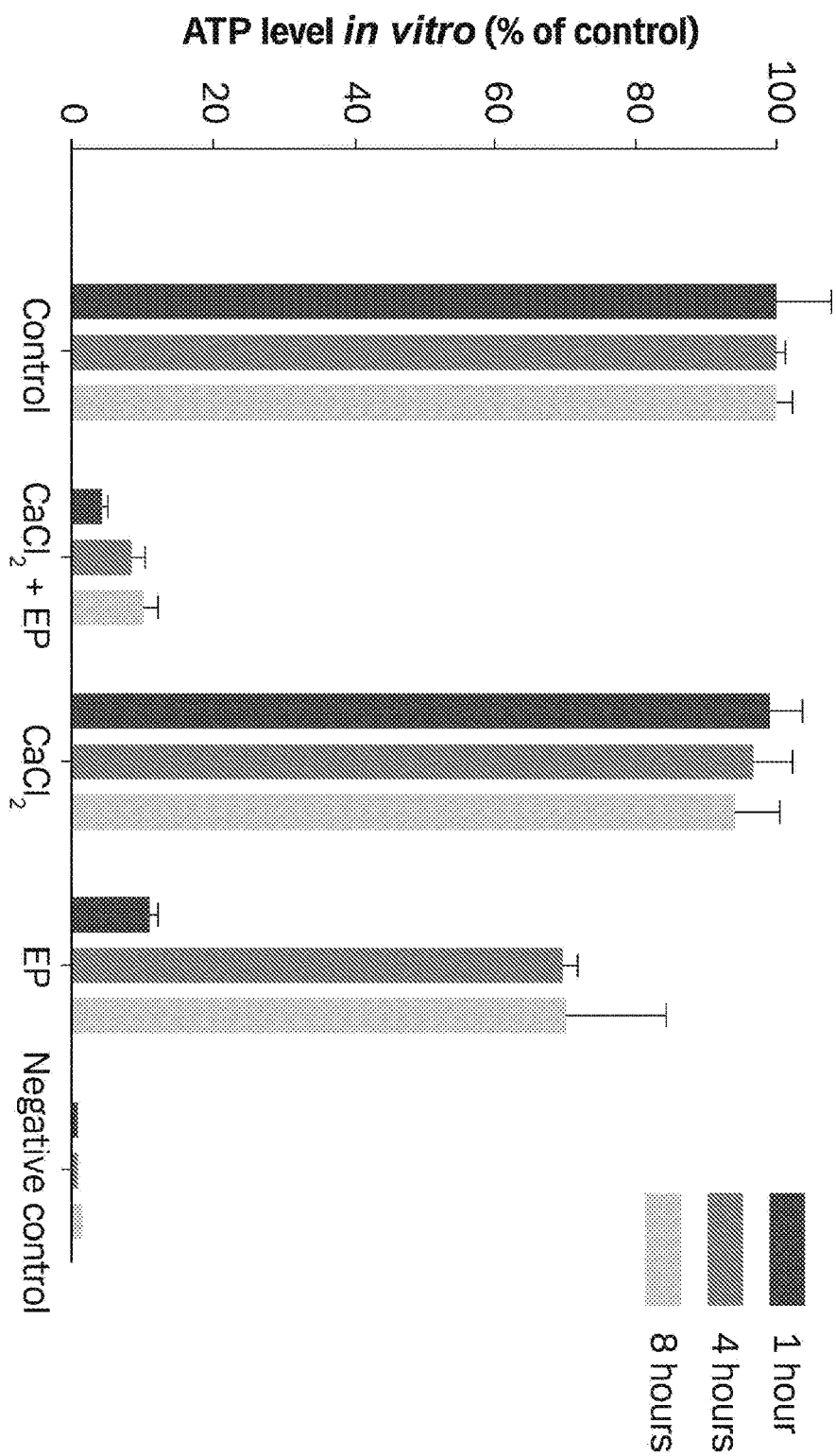

The present inventors' results clearly show that calcium overload induced by calcium electroporation results in severe ATP depletion and necrosis see e.g. FIG. 6-8.

The present inventors have tested several ratios between the administrated or injected calcium containing solutions versus the volume of the neoplasm in order to identify the effect of variances in such ratios, especially in in vivo settings, and surprisingly discovered that a normal 1 to 1 ratio between the neoplastic volume and the infused calcium solution did in fact generate a necrotic effect on the healthy tissues surrounding the neoplasm, where as a reduction of the ratio to 0.5 as shown in Example 3 maintained the desired necrosis in the neoplastic cells without creating necrosis in the surrounding tissue.

Thus, in one embodiment, the present invention relates to a ratio of the volume of the solution of the present invention when compared with the volume of the part of the neoplasm where the method of the present invention is applied in a range of 0.2 to 0.8. The ratio between 0.2 and 0.8 includes sub-ranges, such as but not limited to 0.3 and 0.7, 0.4 and 0.6 or 0.45 and 0.55 or 0.2 and 0.7 or 0.2 and 0.5 and so on and so forth. In a preferred embodiment the ratio is in the range of 0.4 to 0.6.

The neoplastic volume is generally calculated $V=a \times b^2 \times n/6$ where "a" is the largest diameter of the neoplasm and "b" is the largest diameter perpendicular to "a", or calculated $V=l \times w \times h \times n/6$, where "l" is the length, "w" is the width and "h" is the height of the neoplasm.

Thus, the use of the concentration and volume chosen at the time of the preinclusion visit should be evaluated with the corresponding modality treatment, and the neoplasms to be treated, should at least be measured and the volume calculated by one of the above mentioned formula and then the dose to be injected should be estimated, with a volume according to the present invention in each neoplasm.

Means for Causing Transient Permeabilisation

The inventors of the present invention have demonstrated that the potential advantages compelling from a biophysics perspective, that $Ca^{++}$ will readily pass through even the smallest pore size effected by the transient permeabilisation, about 1 nm is widely accepted in the field. This means that pores need not expand to transport $Ca^{++}$ and therefore a wide range of transient permeabilisation means may be considered before, during and/or after the administration of the calcium ions.

Thus, the present invention relates to any means of causing transient permeabilisation.

In an embodiment transient permeabilisation relates to transient permeabilisation of cell membranes.

In one embodiment the means for causing transient permeabilisation is selected from the group consisting of electroporation, sonoporation, hydrodynamics-based procedures and magnetic induction, including but not limited to, fields induced by equipment for performing magnetic resonance scans (MR). The example section shows data for both electroporation and sonoporation.

Magnetic Resonance

Magnetic resonance is typically divided into Nuclear magnetic resonance, Electron spin resonance, Magnetic resonance imaging (MRI), Functional magnetic resonance imaging (fMRI), and Muon spin spectroscopy (I-lSR). All types apply to the present invention.

In one embodiment the means for transient permeabilisation is magnetic resonance.

Electroporation

In a presently preferred embodiment the means for transient permeabilisation is electroporation. Any given electrode may be used, such as but not limited to aluminum or stainless steel. The waveform of the electrical pulses can be selected for a wide range. The optimal waveform might vary between different settings and this approach appears very flexible. In most cases electroporation (EP) is performed by inserting arrays of needle electrodes (see example 5) and delivering pulsed electrical fields emanating from these electrodes directly to the cancerous cell mass. Electroporation can also be applied by other electrodes, such as but not limited to plate electrodes, see example 3. Pulse parameters are generally within the following ranges: field strength 200-2000 V/cm; pulse length 0.1-10.0 ms; pulse number 2-20; and pulse frequency 1 Hz-5 kHz.

Short, high voltage pulse range; 8 pulses of 0.1 ms, 0.5-1.3 kV/cm (voltage to electrode distance ratio), 1 Hz-5 kHz Ultrashort (nanosecond), high voltage pulse range; 100 to 400 pulses of 10 to 30 ns, up to 35 MV/m, at 50 Hz Low voltage pulse range; 8-10 pulses of 2-400 ms, voltage 20-140 Vjcm freq. 0.5-10 Hz Applying such electric fields result in permeabilisation of cell membranes, this allows anticancer drugs such as calcium ions to enter cells and to cause the required necrotic effect due to the drug uptake. The effect is not observed in the absence of electroporation.

Electroporation based therapies (EPT) have been shown to be effective against many types of solid tumors in animals and several types of tumors in humans. In fact, several clinical studies have been completed or are presently ongoing.

Electroporation may be performed using a wide range of pulse characteristics. Pulse shapes includes, but is not limited to, exponential, square wave, ramped pulse shapes. Anywhere from 1 to multiple pulses may be used in various sequences, and pulse amplitudes may vary from e.g. 20 V/cm (voltage to electrode distance ratio) to 35 MV/m and with pulse durations from the picosecond or nanosecond range, to the micro- or millisecond range. Finally, the pulsing frequency may range from 0.5 Hz to e.g. 5 kHz.

The combination of parameters is important to secure optimal permeabilisation of the cell membrane without destroying the cell. The pulses can be but not limited to short, high voltage pulses, very short, very high voltage pulses (nanosecond pulse electroporation), or long, low voltage pulses. Pulse combinations resulting in no membrane regeneration is irreversible electroporation which can also be used in the present invention for permeabilisation of cell membranes.

The present inventors have used short, high voltage pulses in the in vitro and in vivo examples (see example 1, 3 and 5). These pulses induce transient permeabilisation of cell membranes.

In one embodiment the present invention relates to 1 or more pulses, 20 V/cm to 100 kV/cm, 10 ns to 400 ms and a frequency of 1 to 60 kHz.

Waveform may be square, exponential or ramped or any other form.

In one embodiment the present invention relates to transient permeabilisation caused by electroporation with 8 pulses of 1.0 kVjcm for 100 IJS and a frequency of 1 Hz.

Nanosecond Pulsed Electric Fields

The application of pulsed electric fields with nanosecond durations (10 to 300 ns) and high intensity (up to 35 MV/m)—called nanopulses, nsPEFs, or nanoelectropulses is also suitable for the present invention. One of the advantages with nanopulses is that they are non-ionizing and do not cause significant heating.

Nanopulses can disrupt cell membrane integrity. Theoretical analysis and empirical data suggest that the effects of nanoelectropulses on biological systems are different from those of classical electroporative pulses. Nanosecond pulses of sufficient amplitude permeabilise intracellular membranes in addition to the plasma membrane and produce nuclear changes not observed with longer, lower-field pulses. Nanopores allow the passage of small inorganic ions.

Sonoporation

Sonoporation, or cellular sonication, in the present context is the use of sound (typically ultrasonic frequencies) for modifying permeability of the cell membrane, such as but not limited to ultrasound mediated membrane permeabilisation. Studies have shown that applied appropriately ultrasound can permeabilise viable cells reversibly so that exogenous material can enter cells without killing them.

This technique is used in molecular biology and non-viral gene therapy in order to allow uptake of large molecules such as DNA into the cell, in a cell disruption process called transfection or transformation. The technique has also been shown to increase transport of small drugs across skin.

Sonoporation employs the acoustic cavitation of microbubbles to enhance delivery of large molecules. Acoustic cavitation involves the creation and oscillation of gas bubbles in a liquid. During the low-pressure portion of an ultrasound wave, dissolved gas and vaporized liquid can form gas bubbles. These bubbles then shrink and grow in size, oscillating in response to the subsequent high- and low-pressure portions of the ultrasound wave. This is referred to as stable cavitation. Cavitation is believed to be responsible for ultrasonic permeabilisation of cells and tissues of interest. To develop protocols useful for drug delivery, the effects of ultrasound parameters on cavitation and cell membrane permeabilisation need to be well established. The bioactivity of sonoporation has similarities with electroporation. In example 12 sonoporation has been used with very good results.

A sonoporation scheme may be 3.5 Wjcm2 at 1 MHz and 100% duty cycle for 2 minutes. Thus, in one embodiment the means for transient permeabilisation is sonoporation.

Hydrodynamics-Based Procedures

Hydrodynamic delivery employs a physical force generated by a rapid injection of large volume of solution into e.g. a vasculature to facilitate transfer. This method has been shown capable of introducing molecules to cells. Hydrodynamics-based gene delivery, involving a large-volume and high-speed intravenous injection of naked pDNA, gives a significantly high level of transgene expression in the liver and other major organs. This procedure has been used frequently as a simple and convenient in vivo transfection method. The principle of the hydrodynamics-based procedure could be applicable to an organ-restricted gene delivery method; i.e. targeting to organs such as the liver, the kidney and the hindlimb muscles by injection via a suitable vein or artery with transient occlusion of the outflow as demonstrated previously. In spite of the frequent use of the hydrodynamics-based procedure in functional studies of therapeutic genes or DNA elements, little is known about the mechanisms underlying efficient gene transfer by this procedure.

It has been demonstrated that rapid injection and a large volume of pDNA solution were required to obtain a high level of transgene expression, indicating that a high blood pressure was the most critical factor for the gene transfer efficiency.

Hydrodynamics-based procedures can also be used for delivering other drugs and molecules. Thus this technique can be used in the present invention.

In one embodiment the means for transient permeabilisation is hydrodynamic delivery.

Induce Necrosis

Necrotic tissue does not undergo the same chemical reactions as apoptotic dying tissue does. Cancer cells are often more resistant to apoptosis, due to changes in the pathways governing apoptosis (up- or downregulation of key elements in the pathways associated with apoptosis). In tissue damage leading to necrosis (apoptosis independent pathways), cancer cells do not seem less sensitive to cell death than normal cells.

The present inventors have disclosed that the standard apoptotic effects of $Ca^{++}$ loading by electroporation is not sufficient to kill the tumors 100% and thereby avoid relapses, since many tumor cells have some resistance to apoptosis.

Every cell in a multicellular organism has the potential to die by apoptosis, but tumor cells often have faulty apoptotic pathways. These defects not only increase tumor mass, but also render the tumor resistant to therapy inducing apoptosis. Thus, as disclosed by the present inventors killing tumor cells by necrosis increases the rate of complete removal of the tumors—as the tumor cells have no resistance mechanisms against necrosis.

Thus, therapy inducing necrosis will secure higher success rates of tumor removal in the clinic, and is thus a presently preferred object of the present invention. The present invention is furthermore somewhat unique among the many methods employed for local and regional tumor control in that it is very effective and causes few if any side effects. Results shown herein from both in vitro as well as in vivo animal and human studies indicate the present invention effectively destroys most tumors via necrotic mechanisms while causing only a minor effect (inflammation, minor necrosis) on normal tissues surrounding the tumor (example 17), particularly when concentration, doses volume, and pulse parameters are within appropriate ranges as described herein.

Cells can undergo different types of cell death such as necrosis and apoptosis. Necrosis is normally described as non-programmed cell death and apoptosis as programmed cell death. Necrosis begins with an impairment of the cell's ability to maintain homeostasis, leading to an influx of water and extracellular ions. Intracellular organelles, most notably the mitochondria, and the entire cell swell and rupture (cell lysis). Due to the ultimate breakdown of the plasma membrane, the cytoplasmic contents including lysosomal enzymes are released into the extracellular fluid. Thus, the characteristic morphological and biochemical features of necrosis include loss of membrane integrity, swelling of cytoplasm, mitochondria, and organelles, cell lysis, and no vesicle formation. Apoptosis, in contrast, is a mode of cell death that occurs under normal physiological conditions and the cell is an active participant in its own demise ("cellular suicide"). The characteristic morphological and biochemical features of apoptosis include chromatin aggregation, nuclear and cytoplasmic condensation, partition of cytoplasm and nucleus into membrane bound-vesicles (apoptotic bodies) which contain ribosomes, morphologically intact mitochondria and nuclear material. Due to the different morphological features of apoptosis and necrosis a pathologist can determine the type of cell death the cells in a tissue undergo. Thus, it is clear that the present invention relates to a method that induces necrosis.

Thus, in one embodiment, the present invention relates to a method wherein the calcium ions induce necrosis in at least 30% of the part of the neoplasms exposed to said means for causing transient permeabilisation of the cell membranes, such as at least 40%, such as but not limited to at least 50% of the neoplasms, such as at least 60% of the neoplasms, such as at least 70% of the neoplasms, such as at least 75% of the neoplasms, such as at least 80% of the neoplasms, such as at least 85% of the neoplasms, such as at least 88% of the neoplasms, such as at least 89% of the neoplasms, such as at least 90% of the neoplasms, such as at least 91% of the neoplasms, such as at least 92% of the neoplasms, such as at least 93% of the neoplasms, such as at least 94% of the neoplasms, such as at least 95% of the neoplasms, such as at least 96% of the neoplasms, such as at least 97% of the neoplasms, such as at least 98% of the neoplasms, such as at least 99% of the neoplasms.

In a presently preferred embodiment, the neoplasm is a solid tumor.

Tumor Size

Shown herein is that injecting calcium-chloride in tumors in mice with an average diameter of 6.2 mm was highly efficient. Tumors such as but not limited to solid tumors can vary in size from a few millimeters to several centimeters and the present inventors have clinically observed effective treatment with electrochemotherapy of tumors that measured over 25 cm in diameter.

Since electrochemotherapy has proven efficient in very large tumors the present invention is likely effective in all tumor sizes from 0.5 cm in diameter to over 25 cm in diameter.

Tumors less than 0.5 cm in diameter have small volumes complicating successful injection of the solution in the tumor without injection in the normal tissue.

Tumors can vary in spatial form and thereby differ in volume even with the same diameter. Basal cell carcinomas are usually flat tumors, thereby having a small volume (a tumor of 0.5 cm in diameter and 0.2 cm in height has a volume of 0.03 cm$^3$), whereas a round tumor will have a larger volume (a round tumor of 0.5 cm in diameter has a volume of 0.07 cm$^3$).

Thus, in one embodiment the present invention relates to a method according the present invention wherein the solid tumor has a minimum diameter of 0.5 cm.

Shown herein is that intratumoral injection of calcium chloride in tumors in mice was highly effective. Intratumoral injection or infusion of calcium solutions secures high calcium concentrations in the selected area with few or none effects elsewhere. Intravenous injection of calcium solutions is not likely to result in sufficiently high calcium concentrations in the tumor area due to adsorption to plasma proteins. Intravenous injection of calcium solutions is also limited due to the risk of hypercalcemia.

Thus, in one embodiment the present invention relates to a method wherein solution is administrated by intratumoral injection or infusion.

Rate of Injection and Pressure—Recreate Experiments

The injection rate has to be fast due to diffusion and washout of calcium to the surrounding tissue and the blood stream. The inventors have injected the calcium solution within 30 seconds to secure high calcium concentration in the treated area when applying the means for causing transient permeabilisation of cell membranes.

General

Reference to any prior art in this specification is not, and should not be taken as, an acknowledgment or any form of suggestion that this prior art forms part of the common general knowledge in any country.

All patent and non-patent references cited in the present application, are hereby incorporated by reference in their entirety.

As will be apparent, preferred features and characteristics of one aspect of the invention may be applicable to other aspects of the invention. The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced by reference therein.

It should be understood that any feature and/or aspect discussed above in connection with the methods according to the invention apply by analogy to the use of the solution of the present invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention will hereinafter be described by way of the following non-limiting Figures and Examples.

FIGURE LEGENDS

FIGS. 1-2

Calcium Overloading Induces Cell Death In Vitro

Figure 2:
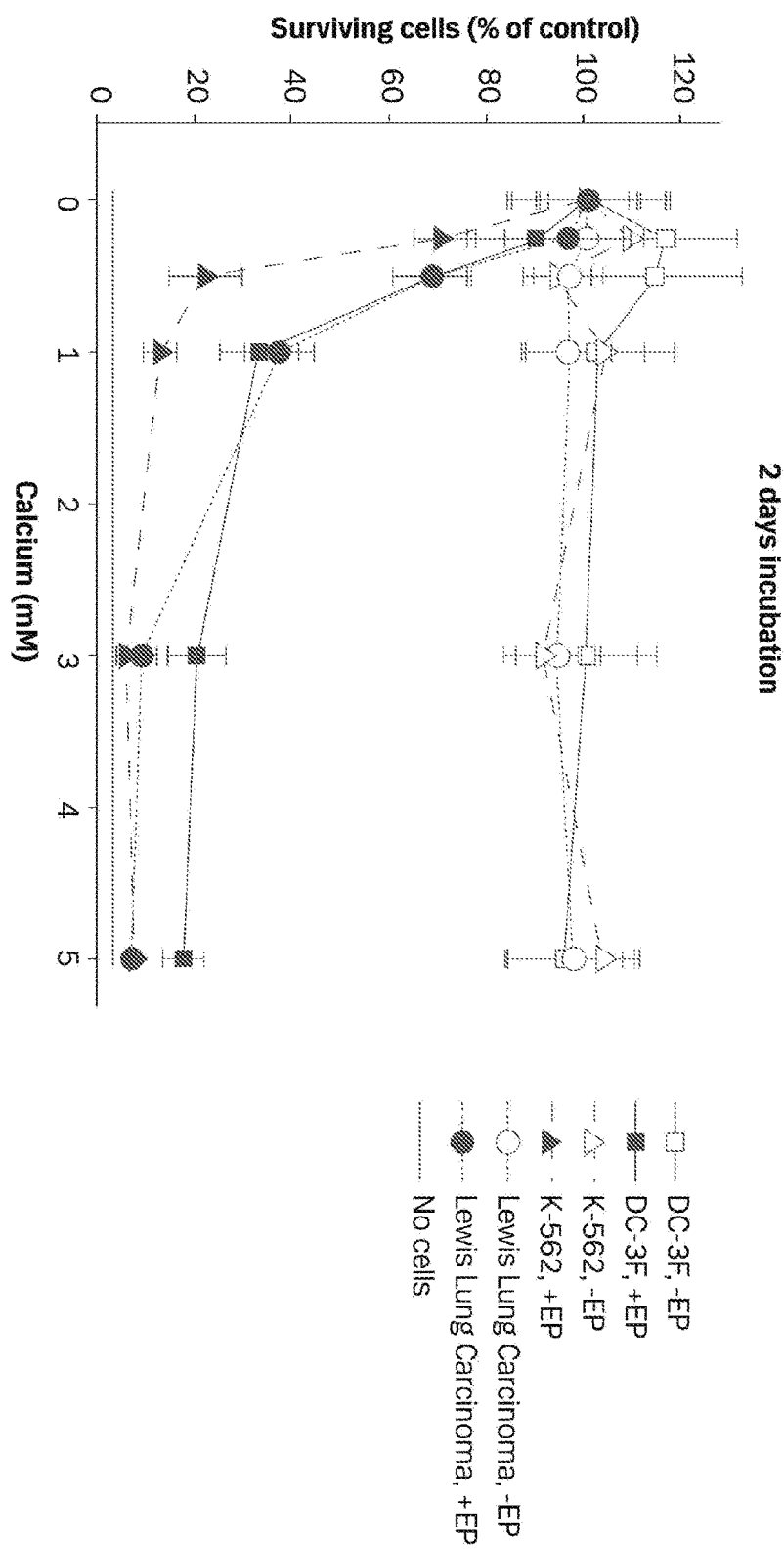

Cell viability in three cell lines, DC-3F, a transformed Chinese hamster lung fibroblast cell line (■), K-562, a human leukemia cell line (▲), and Lewis Lung Carcinoma, a murine lung carcinoma cell line (●) after treatment with increasing calcium concentrations either electroporated (black) or not electroporated (white). MTT viability assay was performed respectively 1 (FIG. 1) and 2 days (FIG. 2) after treatment. Results are depicted as percentages of controls (electroporated or non-electroporated cells in 0 mM calcium) (means±s.d., n≥6). EP, electroporation.

FIGS. 3-4

Calcium Overloading Induces Cell Death In Vivo

H69 (Enhanced Green Fluorescent Protein (EGFP) transfected human small cell lung cancer cell line) tumors induced on nude mice were treated with isotonic calcium-chloride (168 mM) and electroporation (D), calcium-free physiological saline and electroporation (C), isotonic calcium-chloride alone (B), or calcium-free physiological saline alone (A). Tumor size (FIG. 3) and fluorescence intensity in bioimager (FIG. 4) were measured before treatment and 3 times a week after treatment, (means+s.d., n=3-9). EP, electroporation; NC, normalised counts.

FIG. 5

Fluorescence Intensity Images

Representative images of fluorescence intensity in the tumors treated with isotonic calcium-chloride (168 mM) and electroporation, calcium-free physiological saline and electroporation, isotonic calcium-chloride alone, or calcium-free physiological saline alone. Placement of the mouse in the scanner and location of the tumor is shown in the top right corner, intensity bar is shown as a logarithmic scale. EP, electroporation; NC, normalised counts.

FIG. 6

Calcium Overloading Induces Tumor Necrosis

The fraction of necrosis in tumors before treatment, 2 hours, 1, 2, and 6 days after treatment with calcium electroporation determined by stereological point counting, (median, individual data points (▲), n=4 for treated tumors and n=2 for untreated tumors).

FIG. 7

Light Microscope Images

Representative HE-sections of tumors 2 hours, respectively 6 days after calcium electroporation. EP, electroporation.

FIG. 8

Calcium Overloading Induces ATP Depletion

ATP level in DC-3F cells 1 hour (dark grey/left bars), 4 hours (grey/middle bars) and 8 hours (light grey/right bars) after treatment with calcium electroporation, calcium alone or electroporation alone, control (untreated cells), negative control (dead cells). ATP level is shown in percent of control (means+s.d., n=6). EP, electroporation.

FIG. 9

Schematic View of the Effect of Calcium Overloading

Electroporation (EP) generates reversible pores in the cell membrane (1) allowing influx of calcium and sodium, and efflux of potassium and possible also of ATP. Changes in the intracellular ion concentrations lead to high ATP consumption by $Ca^{2+}$-ATPases (in the plasma and endoplasmic reticulum membranes) and $Na^+/K^+$-ATPases (2). Calcium overload may induce permeability transition pore (PTP) opening in the mitochondrial membrane resulting in loss of ATP production due to loss of the electrochemical gradient (3), and activation of lipases and proteases, and generation of reactive oxygen species (ROS) (4). This results in severe ATP depletion and necrosis of the cell.

FIGS. 10-11

Calcium Overloading Induces Necrosis in Various Tumor Types

Calcium overloading induces tumor necrosis in LPB (murine sarcoma) tumors (10A), B16 (murine melanoma) tumors (10B), MDA-MB231 (human breast cancer) tumors (11A), HT29 (human colon cancer) tumors (11B), and in SW780 (human bladder cancer) tumors (11C).

The fraction of necrosis in tumors before treatment, 2 hours, 1, 2, and 6 days after treatment with calcium electroporation was determined by stereological point counting (median, individual data points (▲), n=3-4 for treated tumors and n=2 for untreated tumors).

FIG. 12

Calcium in Combination with Sonoporation Induces Cell Death

CT26 (murine colon carcinoma cell line) tumors induced on Balb/c mice were treated with isotonic calcium-chloride (168 mM) and sonoporation ($CaCl^{2+}$SP), sonoporation alone (SP), isotonic calcium-chloride alone ($CaCl_2$), or untreated. Tumor size were measured before treatment and every second day after treatment, (means+s.d., n=S). SP, sonoporation.

FIG. 13

Calcium Electroporation Using Different Calcium Sources

Cell viability of DC-3F cells (a transformed Chinese hamster lung fibroblast cell line) after treatment with 1 mM calcium chloride (prepared by SAD, Denmark) or 1 mM calcium glubionate (Sandoz, Holzkirchen, Germany) and electroporation (8 pulses of 991-1s, 1 Hz and increasing field strength). MTT viability assay was performed 1 day after treatment. Results are depicted as percentages of untreated controls (means±s.d., n=6).

FIG. 14

Effect of Electroporation with Calcium and Bleomycin

Cell viability of DC-3F cells (a transformed Chinese hamster lung fibroblast cell line), K-S62 cells (a human leukemia cell line) and Lewis Lung Carcinoma (LLC; a murine lung carcinoma cell line) after treatment with 0.25 mM calcium and/or 0.01 µM bleomycin and electroporation with 8 pulses of 99 µs at 1.2 kV/cm (DC-3F and K-562) or 1.4 kV/cm (LLC) and 1 Hz. MTT viability assay was performed 2 days after treatment. Results are depicted as percentages of controls electroporated without calcium and bleomycin (means+s.d., n=6).

FIG. 15

Calcium Electroporation of Canine Tumor

Pictures showing a canine tumor on the heel joint of a 7 year old Danish Pointer Dog before treatment and 1 day and 11 days after treatment with 168 mM calcium chloride in a total volume equivalent to 50% of the tumor volume and electroporation.

FIG. 16

Calcium Electroporation of Brain Tumor

N32 (a rat brain glioma derived tumor cell line) tumors induced in rat brains are treated with calcium alone (14 µl, 168 mM) or calcium electroporation (14 µl 168 mM calcium chloride and 32 pulses of 100V for 100 µs and 1 Hz). MRI is performed before treatment and at day 1, 6, and S after the treatment. Light microscope images of H&E stained sections of the tumors after termination of the experiment is also shown.

FIG. 17

Normal Tissue Response—Skin

MDA-MB231 (a human breast cancer cell line) tumors induced on nude mice were treated with calcium chloride (100-500 mM calcium and injection volume equivalent to 20%-80% of the tumor volume) and electroporated or not, treated with physiological saline and electroporated or not, or untreated but with needle inserted in the tumor without injection and with electrodes put on the tumor without pulses applied. Seven days after the treatment corebiopsies of the skin above the tumor were formalin fixed, paraffin-embedded and the presence of inflammation was estimated in H&E stained sections of the skin. The presence of inflammation in the skin dermis and subcutis was scored from 1-3 (1=minimal, 2=moderate and 3=severe). The results are presented as mean+s.d., n=5-6.

FIG. 18

Normal Tissue Response—Muscle

MDA-MB231 (a human breast cancer cell line) tumors induced on nude mice were treated with calcium chloride (100-500 mM calcium and injection volume equivalent to 20%-80% of the tumor volume) and electroporated or not, treated with physiological saline and electroporated or not, or untreated but with needle inserted in the tumor without injection and with electrodes put on the tumor without pulses applied. Seven days after the treatment the muscle located below the tumor was formalin fixed, paraffin-embedded and the fraction of necrosis was estimated in H&E stained sections of the muscle. The results were grouped into 3 groups (0=no necrosis, 1=scattered, solitary necrotic myocytes, 2=focal areas of coagulation necrosis). The results are presented as mean+s.d., n=s–6.

EXAMPLES

Example 1

In Vitro Electroporation
Materials and Methods

Three cell lines are used for in vitro experiments, DC-3F, a transformed Chinese hamster lung fibroblast cell line; K-562, a human leukemia cell line; and Lewis Lung Carcinoma, a murine lung carcinoma cell line. DC-3F cells were tested for mycoplasma in January 2011, K-562 cells were tested for mycoplasma in 2008 prior to freezing and thawing just before experiments were performed, and Lewis Lung cells were tested by rapid MAP27 panel (Taconic, Hudson N.Y.) in July 2011 without signs of infection. Cells are maintained in RPMI 1640 culture medium (GIBCO™, Life Technologies, Carlsbad, Calif.) with 10% fetal calf serum (GIBCO™, Life Technologies, Carlsbad, Calif.), penicillin and streptomycin at 37° C. and 5% C02. After harvesting, cells are washed and diluted in HEPES buffer containing 10 mM HEPES (Lonza, Basel, Switzerland), 250 mM sucrose and 1 mM $MgCl_2$ in sterile water. 270 µl cell suspension ($6.1\times10^6$ cells/ml) and 30 µl $CaCl_2$, or in the case of controls, HEPES buffer, are electroporated in 4 mm wide cuvettes with aluminium electrodes (Molecular BioProducts, Inc., San Diego, Calif.). Cooled cells (8° C.) are exposed to 8 pulses of 1.2 kV/cm with pulse duration of 99 µs (DC-3F and K562 cells) or 8 pulses of 1.4 kV/cm with pulse duration of 99 µs (Lewis Lung Carcinoma) using a BTX® T820 square wave electroporator (BTX®, Harvard Apparatus, Holliston, Mass.). The electroporation parameters are chosen after optimization to obtain high permabilisation and cell survival. After 20 min at 37° C. and 5% $CO_2$ cells are diluted in RPMI 1640 culture medium with 10% fetal calf serum and penicillin-streptomycin and seeded in 96-well plates at a concentration of $3.1\times10^4$ cells/100 µl. After respectively 1 and 2 days incubation MTT assay is performed using a MULTISKAN® ASCENT® ELISA reader (Thermo Lab-systems, Philadelphia, Pa.).

Difference between electroporated and non-electroporated cells in identical buffer is assessed using two-way analysis of variance (ANOVA) with post least-squares-means test with Bonferroni correction for multiple comparisons.

Results

To test the effect of calcium overloading in vitro three cell lines from different species and of different tissue origin (DC-3F, a transformed Chinese hamster lung fibroblast cell line; K-S62, a human leukemia cell line; Lewis Lung Carcinoma, a murine lung carcinoma cell line) were electroporated in buffers containing increasing calcium concentrations (0 to SmM). Cell viability was determined respectively 1 (FIG. 1) and 2 (FIG. 2) days after treatment. This shows that calcium electroporation, induces dose dependent cell death in all three cell lines. In contrast, incubation at high calcium concentrations has no effect on cell viability in non-electroporated cells. There is a dramatic decrease in viability for all electroporated cell lines with $EC_{50}$ being 0.57 mM $Ca^{2+}$ (range 0.35-0.79 mM) whereas $EC_{50}$ is not reached without electroporation. Viability decreases significantly ($p<0.01$) starting from 0.5 mM for all cell lines treated. As expected, due to differences in e.g. cell size and homogeneity there is a differential effect of the electroporation procedure alone on the different cell lines, as electroporation in buffer without calcium reduce viability by respectively 0% (DC-3F), 6% (Lewis Lung Carcinoma) and 23% (K-562). Consequently, values are listed as a percentage of electroporated respectively non-electroporated controls. The decrease in viability after calcium electroporation is similar to the effect induced by electroporation with the chemotherapeutic agent bleomycin in concentrations from 0.1 µM (data not shown).

Example 2

ATP Assay
Materials and Methods

DC-3F cells are electroporated as described in Example 1 with 1 mM calcium. Cells electroporated with HEPES buffer, non-electroporated cells with 1 mM calcium, and untreated cells are used as controls. Cell death induced by irreversible electroporation (8 pulses of 6.6 kV/cm with pulse duration of 99 µs) is used as negative control. Cells are seeded in 96-well plates at a concentration of $3.1\times10^4$ cells/100 µl. Cells are lysed using Cell-Based Assay Lysis Buffer (Cayman Chemical, Ann Arbor, Mich.) and ATP content is determined after 1, 4 and 8 hours incubation by adding 100 µl rL/L Reagent (ENLITEN® ATP assay, Promega, Madison, Wis.) and measuring light emission using a luminometer (LUMIstar®, BMG biotechnology, Ortenberg, Germany).

Difference in ATP level after different treatments is assessed using two-way ANOVA with post least-squares-means test with Bonferroni correction for multiple comparisons.

Results

Since Calcium electroporation ($Ca^{2+}$-EP) treatment leads to highly efficient cell death independently in different cell lines and also leads to uniform necrosis across tumors within 6 days (see Example 4), a condition fundamental for cell survival must be involved. Previous work from this group showed that ATP decreased significantly in tissue exposed to high voltage pulses. Determination of ATP levels in tumor cells after treatment show that $Ca^{2+}$-EP treatment results in an immediate and severe drop in ATP level, which stays low, at 10.3% ($p<0.0001$) of control levels up to 8 hours after treatment (FIG. 8). Cells treated with electroporation alone exhibit a similar drop in ATP level but with a marked recovery 4 hours after treatment to levels significantly higher than $Ca^{2+}$-EP treated cells (p<0.0001). Calcium without electroporation does not affect ATP levels. Cells electroporated with calcium-free physiological saline show a similar drop and recovery in ATP level as cells treated with electroporation alone (data not shown).

Figure 4:
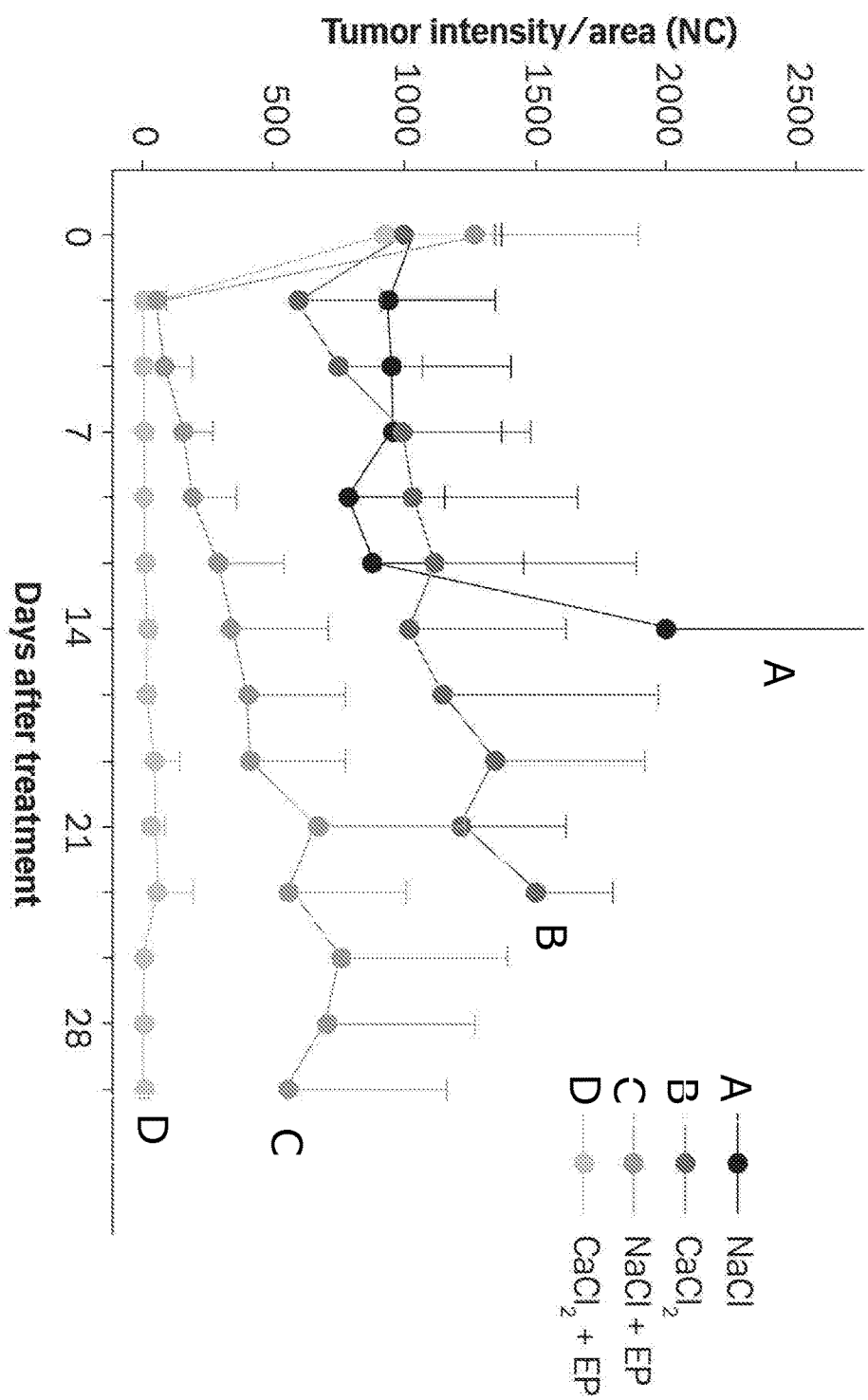
Figure 9:
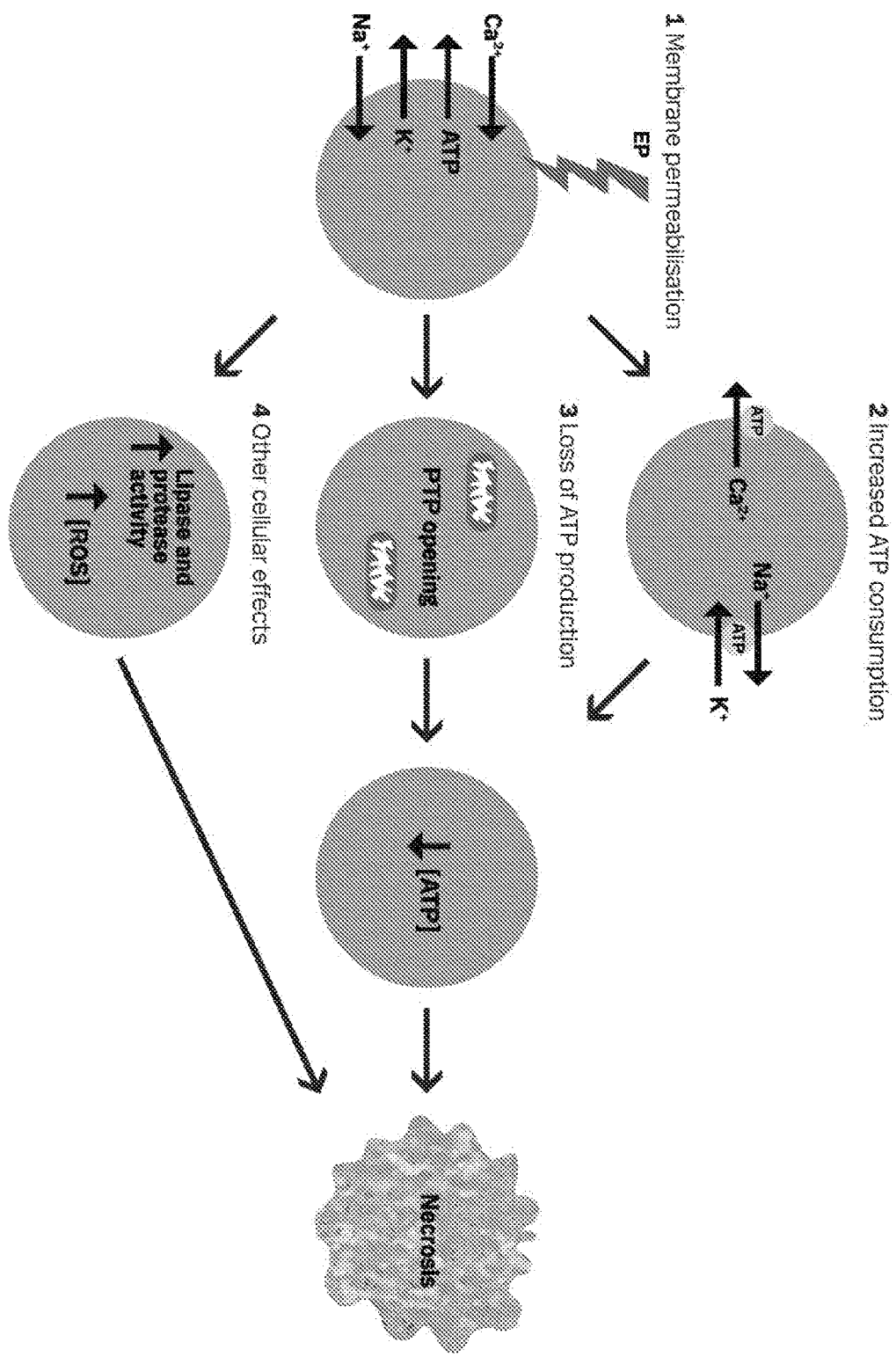

Here we show that calcium electroporation leads to acute ATP depletion and cell death (in vitro) as well as massive tumor necrosis in vivo (Example 4). As illustrated in FIG. 9, ATP depletion in relation to raised intracellular levels of free calcium may be caused by greatly increased activity of the $Ca^{2+}$-ATPase leading to high consumption of ATP. Furthermore, a high intracellular calcium level may induce opening of permeability transition pores (PTP) in the mitochondrial membrane, resulting in loss of the electrochemical gradient, the driving force for ATP production, thereby uncoupling mitochondrial formation of new ATP. Other cellular effects associated to calcium overload include activation of lipases and proteases, and generation of reactive oxygen species (ROS), which may also contribute to cell death. Finally, the electroporation procedure itself may lead to increased ATP consumption as the influx of sodium (either directly or due to sodium calcium exchange) may increase the activity of the $Na^+/K^+$-ATPase. Furthermore, a direct loss of ATP through the permeabilisation structure is also a possible contributor. Altogether, this may result in cell damage and cell death (FIG. 4). Severe calcium overload causes cell death. Depending on the cellular ATP level, cells undergo either apoptosis or necrosis. If the majority of the mitochondria remain capable of ATP synthesis, the ATP loss may have a transient nature favouring the apoptotic pathway. On the other hand, if the ATP depletion is too severe for apoptosis to occur, the cell will undergo necrosis.

Example 3

Tumor Volume and Tumor Intensity
Materials and Methods

In vivo experiments are performed in accordance with European Convention for the Protection of Vertebrate Animals used for Experimentation and with approval from the Danish Animal Experiments Inspectorate.

H69, a human small cell lung cancer cell line stably transfected with EGFP regulated by the cytomegalo-virus (CMV) promoter, is used for the in vivo experiments. The cells were tested by rapid MAP27 panel (Taconic, Hudson N.Y.) before use without signs of infection. Cells are maintained in vitro as described in Example 1. $1.5 \times 10^6$ cells/100 µl PBS are injected subcutaneously in both flanks of NMRI-Foxn1$^{nu}$ mice (Harlan, Indianapolis, Ind.) that are 9-11 weeks old. Tumor pieces are transplanted from donor mice to the right flank of nude mice. HYPNORM™-DORMICUM™ (fentanyl/fluanisone/midazolam; VetaPharma, Leeds, U K and Roche, Basel, Switzerland) is used for anesthesia complemented with RIMADYL® (Carprofen) (Pfizer ApS, Ballerup, Denmark) as well as lidocaine (Region Hovedstadens Apotek, Herlev, Denmark) in the incision. Mice are randomised at an average tumor size of 6.2 mm (range 5.5-6.9 mm) in largest diameter and tumors are treated with 1) injection of isotonic calcium-chloride solution (168 mM $CaCl_2$) and electroporation (8 pulses of 1.0 kv/cm for 100 µs and a frequency of 1 Hz) using a 6 mm plate electrode and a square wave electroporator (CLINIPORATOR®, IGEA, Modena, Italy), 2) calcium-free physiological saline injection and electroporation (same parameters as above), 3) injection of isotonic calcium-chloride, or 4) calcium-free physiological saline injection. It is confirmed by atomic absorption spectrophotometry (SOLAAR AAS spectrophotometer, Thermo Fisher, Tewksbury, Mass.) that no calcium is present in the physiological saline used (data not shown). Tumor volume is calculated as $ab^2n/6$, where "a" is the largest diameter and "b" is the largest diameter perpendicular to "a". Initially, tumors are injected with a volume equivalent to the tumor volume but as the $Ca^{2+}$-EP group shows skin necrosis, the injected volume is changed to half of the tumor volume for all the groups. The solutions are injected through the side of the firm tumor and the needle is moved around inside the tumor to secure injection all over the tumor. Tumor size measurements using a Vernier caliper and bioimaging scanning using the OPTIX®OPTIX®® MX-2 optical molecular image system (ART, Saint-Laurent, Quebec, Saint-Laurent, Quebec) with a scan resolution of 1.5 mm are performed before treatment and three times a week after treatment. Background fluorescence is measured on the opposite flank and then the background fluorescence level is subtracted from fluorescence intensity of tumors. Finally, all fluorescence intensity below 100 normalised counts (NC) is filtered away using ART, Saint-Laurent, Quebec OPTIX® Optiview version 2.02 software (ART, Saint-Laurent, Quebec).

The differences in tumor volume and fluorescence intensity between tumors in the 4 treatment groups are evaluated as repeated measurements, validated and analysed with an exponential decrease model with Bonferroni correction for multiple comparisons using SAS® software version 9.1 (SAS, Cary, N.C.). 'Group', 'days' and 'mouse' are considered as factors and baseline levels of tumor volume or fluorescence intensity are used as covariant. The fluorescence intensity values are log transformed before the analysis.

Results

Figure 3:
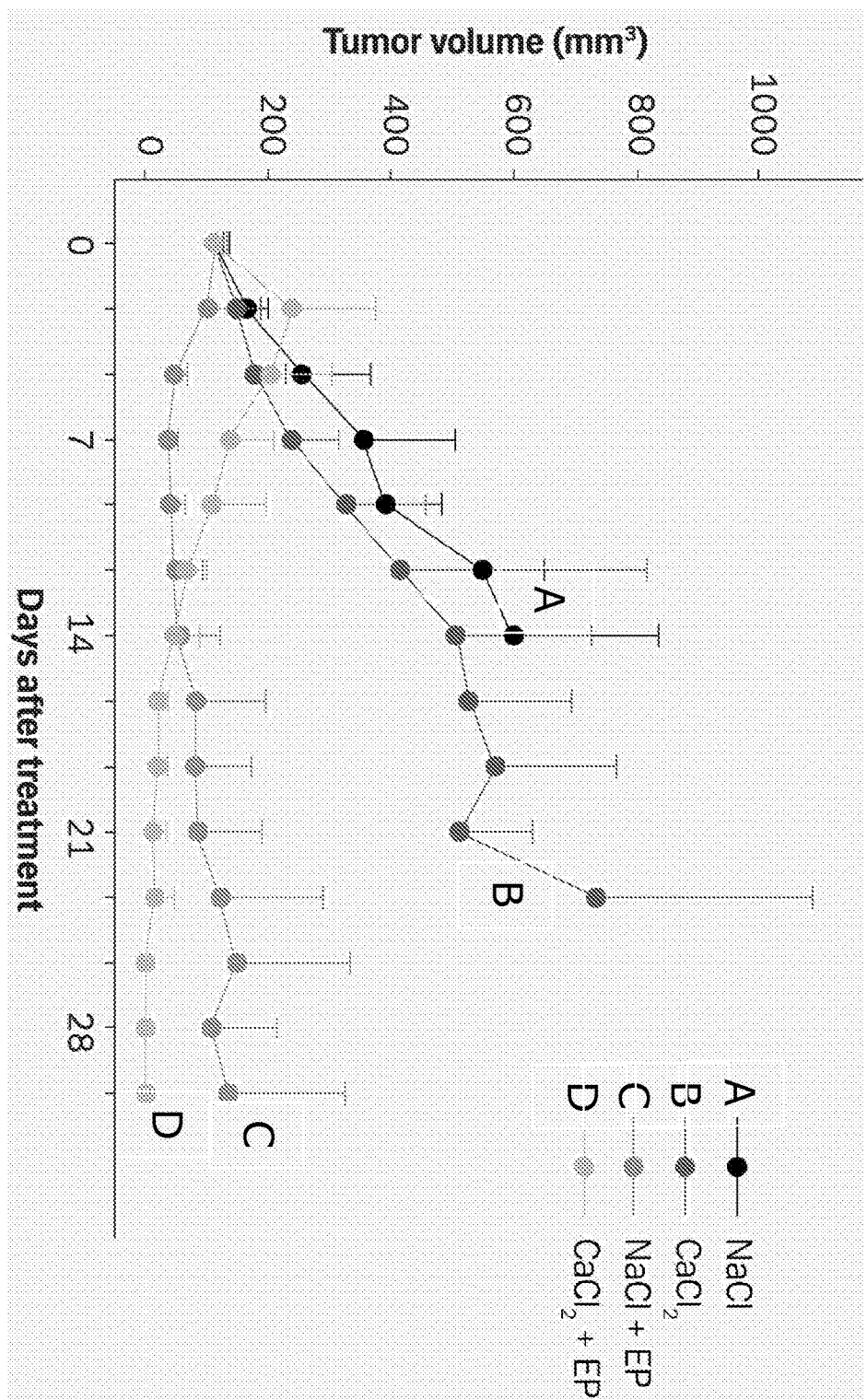

After showing a robust anti-cancer effect in vitro, the effect of calcium electroporation in vivo is tested. Fluorescent H69 tumors, a human small cell lung cancer cell line are treated with an isotonic calcium-chloride injection and electroporated ('$Ca^{2+}$-EP') or in the case of controls, injected with calcium-free physiological saline and electroporated ('NaCl-EP'), or injected with isotonic calcium-chloride ('$Ca^{2+}$') or calcium-free physiological saline ('NaCl') without electroporation (FIG. 3). Strikingly, $Ca^{2+}$-EP treatment eliminates 89% (8/9) of the treated tumors. Ulceration occurs in all $Ca^{2+}$-EP treated tumors, with healing at an average of 18 days (range 9-24 days). Tumor volume is measured including the ulceration, giving the impression that tumor volume is increasing just after treatment, however, fluorescence intensity shows acute decrease in activity after treatment. Volume of tumors treated with $Ca^{2+}$-EP is significantly different from control tumors treated without electroporation (p<0.0001) as well as from tumors treated with NaCl-EP (p<0.01). In all non-electroporated tumors volume continues to increase with a doubling time of respectively 3.9 days (NaCl) and 6.3 days ($Ca^{2+}$). Tumors treated with NaCl-EP decrease in size in the first days after treatment but started to increase in size again around day 7, except two tumors that were eliminated. This indicates that electroporation alone can modulate tumor growth.

Figure 5:
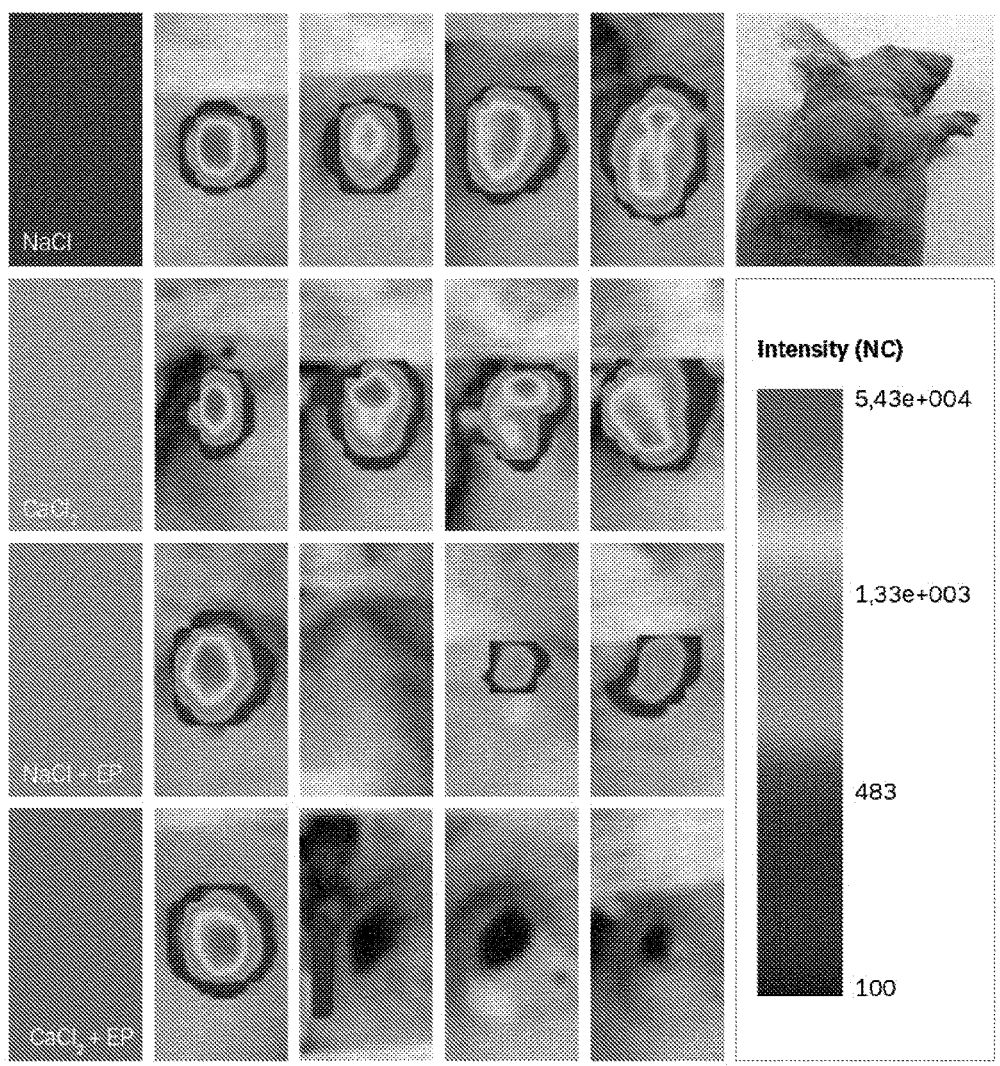

Optical bioimaging is used in vivo to consecutively track the amount of tumor tissue as the H69 tumor cell line is stably transfected with Enhanced Green Fluorescent Protein (EGFP). Fluorescence intensity of $Ca^{2+}$-EP treated tumors decrease drastically after treatment and stay at background levels for the remainder of the experiment, being significantly different from tumors treated with NaCl-EP (p<0.01) and from control groups treated without electroporation (p<0.0001). As expected, fluorescence intensity of the non-electroporated tumors rises over time. The fluorescence intensity of tumors treated with NaCl-EP decreases 2-3 days after treatment and is significantly different from tumors treated with NaCl (p<0.05), thereafter the fluorescence intensity increase and is not significantly different from non-electroporated tumors (FIG. 4-5).

Example 4

Histology
Materials and Methods

At an average tumor size of 6.1 mm (range 5.8-6.6 mm) in largest diameter, the tumors are treated with 168 mM $CaCl_2$ injection and electroporation as described in Example 3. Tumors are removed at skin level before treatment, 2 hours, 1, 2 and 6 days after treatment, fixated in formalin (10% neutrally buffered) and paraffin embedded. Subsequently, tissue sections with a thickness of 3 μm are HE-stained according to the routine procedure of the department. The fraction of necrosis within the tumor is estimated from HE-sections by stereological point counting using a light microscope, evaluated by a pathologist, blinded with respect to treatment status.

The difference in fraction of necrosis is assessed using one-way ANOVA with post least-squares-means test with Bonferroni correction for multiple comparisons.

Results

Histological analysis is performed on tissue sections of formalin-fixed, paraffin embedded tumors treated with $Ca^{2+}$-EP. Sections are stained with hematoxylin/eosin (HE) and the fraction of necrosis is estimated. The analysis of $Ca^{2+}$-EP treated tumors shows progressive necrosis, which is highly significant 2 days after treatment (p<0.0001) and complete 6 days post treatment (FIG. 6-7).

Example 5

Case Study—Applied on Human Patient

In a patient with multiple basocellular carcinomas, where all known treatment options had been tried and the patient was still in need of treatment, calcium electroporation was tried.

In this patient, lesions that were verified by biopsy to contain basocellular carcinoma were treated with different doses of calcium chloride or calcium glubionate with electroporation. Three lesions were treated, measuring 0.8 to 2 cm, by 0.1-0.2 mm deep.

After local anaesthesia (Mir et al), calcium was injected intratumorally using a thin needle and 1 ml syringe. Volumes of resp. 0.1, 0.7 and 3.7 times the calculated tumor volume (in this case calculated as diameter times perpendicular diameter times depth due to the shape of the tumors) was injected.

Immediately after injection (within 45 seconds), electroporation was performed using a square wave pulse generator (CLINIPORATOR®, IGEA, Modena, Italy) and needle electrodes with parallel arrays 0.4 cm apart. Eight pulses of a duration of 0.1 ms and 1 kV/cm (voltage to electrode distance ratio) were administered immediately after calcium injection.

Results showed that efficient tumor cell kill was obtained in the case where the ratio of injected volume was 0.7 with respect to tumor volume (asserted by biopsy), that injecting 0.1 fraction of the tumor volume did not lead to changes (biopsy showed basocellular carcinoma as before treatment), and also that the highest volume of calcium led to necrosis of normal skin (clinical observation), indicating that injected volume of calcium is an important parameter for successful calcium electroporation. Healing of the necrotic area ensued, and patient has been seen subsequently with more than one year of follow-up.

Example 6

Hypothetical Example on Volume Test of Injected Solution
Materials and Methods

In vivo experiments are performed in accordance with European Convention for the Protection of Vertebrate Animals used for Experimentation and with approval from the Danish Animal Experiments Inspectorate.

H69, a human small cell lung cancer cell line stably transfected with EGFP regulated by the cytomegalo-virus (CMV) promoter, is used for the in vivo experiments. The cells are tested by rapid MAP27 panel (Taconic, Hudson N.Y.) before use without signs of infection. Cells are maintained in vitro as described in Example 1. $1.5 \times 10^6$ cells/100 μl PBS are injected subcutaneously in both flanks of NMRI-Foxn1$^{nu}$ mice (Harlan, Indianapolis, Ind.) that are 9-11 weeks old. Tumor pieces are transplanted from donor mice to the right flank of nude mice. HYPNORM™-DORMICUM™ (fentanyl/fluanisone/midazolam; VetaPharma, Leeds, U K and Roche, Basel, Switzerland) is used for anesthesia complemented with RIMADYL® (Carprofen) (Pfizer ApS, Ballerup, Denmark) RIMADYL® (Carprofen) (Pfizer ApS, Ballerup, Denmark) as well as lidocaine (Region Hovedstadens Apotek, Herlev, Denmark) in the incision. Mice are randomised at an average tumor size of 6 mm in largest diameter and tumors are treated with 1) injection of isotonic calcium-chloride solution (16 SmM CaCl2) and electroporation (8 pulses of 1.0 kV/cm for 100 μs and a frequency of 1 Hz) using a 6 mm plate electrode and a square wave electroporator (CLINIPORATOR®, IGEA, Modena, Italy), 2) calcium-free physiological saline injection and electroporation (same parameters as above), 3) injection of isotonic calcium-chloride, or 4) calcium-free physiological saline injection. Tumor volume is calculated as $ab^2n/6$, where "a" is the largest diameter and "b" is the largest diameter perpendicular to "a". Tumors are injected with a volume ratio of 0.2, 0.4, 0.6 or 0.8 compared to the tumor volume. The solutions are injected through the side of the firm tumor and the needle is moved around inside the tumor to secure injection all over the tumor. Tumor size measurements using a Vernier caliper and bioimaging scanning using the OPTIX® MX-2 optical molecular image system (ART, Saint-Laurent, Quebec) with a scan resolution of 1.5 mm are performed before treatment and three times a week after treatment. Background fluorescence is measured on the opposite flank and then the background fluorescence level is subtracted from fluorescence intensity of tumors. Finally, all fluorescence intensity below 100 normalised counts (NC) is filtered away using ART, Saint-Laurent, Quebec OPTIX® Optiview version 2.02 software (ART, Saint-Laurent, Quebec).

The differences in tumor volume and fluorescence intensity between tumors injected with the different solution volumes in the 4 treatment groups are evaluated as repeated measurements, validated and analysed with an exponential decrease model with Bonferroni correction for multiple comparisons using SAS® software version 9.1 (SAS, Cary, N.C.). 'Group', 'days' and 'mouse' are considered as factors and baseline levels of tumor volume or fluorescence intensity are used as covariant.

Results

Calcium electroporation ($Ca^{2+}$-EP) treatment eliminates most of the tumors treated with a volume ratio of 0.2, 004, 0.6 or 0.8 compared to the tumor volume. Ulceration occurs in most of the $Ca^{2+}$-EP treated tumors, with faster healing of tumor treated with volume ratios of 0.2 of the tumor volume compared to tumors treated with volume ratios of 0.8 of the tumor volume. Tumor volume is measured including the ulceration, giving the impression that tumor volume is increasing just after treatment, however, fluorescence intensity shows acute decrease in activity after treatment. Volume of tumors treated with $Ca^{2+}$-EP is significantly different from control tumors treated without electroporation as well as from tumors treated with NaCl-EP for all 4 injection volumes. Tumor volume of all non-electroporated tumors continues to increase for all injection volumes. Tumors treated with NaCl-EP decrease in size in the first days after treatment but tumors start increasing in size for all 4 injection volumes. This indicates that electroporation alone can modulate tumor growth.

Optical bioimaging is used in vivo to consecutively track the amount of tumor tissue as the H69 tumor cell line is stably transfected with Enhanced Green Fluorescent Protein (EGFP). Fluorescence intensity of $Ca^{2+}$-EP treated tumors decrease drastically after treatment and stay at background levels for the remainder of the experiment, being significantly different from tumors treated with NaCl-EP and from control groups treated without electroporation for all 4 injection volumes. Fluorescence intensity of the non-electroporated tumors for all 4 injection volumes rises over time. The fluorescence intensity of tumors treated with NaCl-EP decreases after treatment and thereafter increases for all 4 injection volumes.

Example 7

Hypothetical Example on Concentration Test of Calcium Solution

Materials and Methods

In vivo experiments are performed in accordance with European Convention for the Protection of Vertebrate Animals used for Experimentation and with approval from the Danish Animal Experiments Inspectorate.

H69, a human small cell lung cancer cell line stably transfected with EGFP regulated by the cytomegalo-virus (CMV) promoter, is used for the in vivo experiments. The cells are tested by rapid MAP27 panel (Taconic, Hudson N.Y.) before use without signs of infection. Cells are maintained in vitro as described in Example 1. $1.5 \times 10^6$ cells/100 µl PBS are injected subcutaneously in both flanks of NMRI-Foxn1$^{nu}$ mice (Harlan, Indianapolis, Ind.) that are 9-11 weeks old. Tumor pieces are transplanted from donor mice to the right flank of nude mice. HYPNORM™-DORMICUM™ (fentanyl/fluanisone/midazolam; VetaPharma, Leeds, U K and Roche, Basel, Switzerland) is used for anesthesia complemented with RIMADYL® (Carprofen) (Pfizer ApS, Ballerup, Denmark) as well as lidocaine (Region Hovedstadens Apotek, Herlev, Denmark) in the incision. Mice are randomised at an average tumor size of 6 mm in largest diameter and tumors are treated with 1) injection of calcium-chloride solution and electroporation (8 pulses of 1.0 kV/cm for 100 µs and a frequency of 1 Hz) using a 6 mm plate electrode and a square wave electroporator (CLINIPORATOR®, IGEA, Modena, Italy), 2) calcium-free physiological saline injection and electroporation (same parameters as above), 3) injection of calcium-chloride, or 4) calcium-free physiological saline injection. Four different concentrations of the calcium-chloride solution are used: 100 mM, 220 mM and 500 mM. Tumor volume is calculated as $ab^2n/6$, where "a" is the largest diameter and "b" is the largest diameter perpendicular to "a". Tumors are injected with a volume of half the tumor volume. The solutions are injected through the side of the firm tumor and the needle is moved around inside the tumor to secure injection all over the tumor. Tumor size measurements using a Vernier caliper and bioimaging scanning using the OPTIX® MX-2 optical molecular image system (ART, Saint-Laurent, Quebec) with a scan resolution of 1.5 mm are performed before treatment and three times a week after treatment. Background fluorescence is measured on the opposite flank and then the background fluorescence level is subtracted from fluorescence intensity of tumors. Finally, all fluorescence intensity below 100 normalised counts (NC) is filtered away using ART, Saint-Laurent, Quebec OPTIX® Optiview version 2.02 software (ART, Saint-Laurent, Quebec).

The differences in tumor volume and fluorescence intensity between tumors injected with the different solution volumes in the 4 treatment groups are evaluated as repeated measurements, validated and analysed with an exponential decrease model with Bonferroni correction for multiple comparisons using SAS® software version 9.1 (SAS, Cary, N.C.). 'Group', 'days' and 'mouse' are considered as factors and baseline levels of tumor volume or fluorescence intensity are used as covariant.

Results

Calcium electroporation ($Ca^{2+}$-EP) treatment eliminates most of the tumors treated with calcium chloride solutions above 100 mM. Ulceration occurs in tumors treated with the highest calcium chloride concentrations, whereas no ulceration occurs in tumors treated with the low calcium chloride solution. Tumor volume is measured including the ulceration, giving the impression that tumor volume of tumors treated with the highest calcium chloride concentration is increasing just after treatment, however, fluorescence intensity shows acute decrease in activity after treatment. Tumor volume of tumors treated with all the calcium chloride concentrations decrease in size after treatment. Volume of tumors treated with $Ca^{2+}$-EP is significantly different from control tumors treated without electroporation as well as from tumors treated with NaCl-EP for all calcium chloride solutions. Tumor volume of all non-electroporated tumors continues to increase for all calcium chloride solutions. Tumors treated with NaCl-EP decrease in size in the first days after treatment and start increasing in. This indicates that electroporation alone can modulate tumor growth.

Optical bioimaging is used in vivo to consecutively track the amount of tumor tissue as the H69 tumor cell line is stably transfected with Enhanced Green Fluorescent Protein (EGFP). Fluorescence intensity of $Ca^{2+}$-EP treated tumors decrease drastically after treatment for all calcium chloride solutions and stay at background levels for the remainder of the experiment, being significantly different from tumors treated with NaCl-EP and from control groups treated without electroporation. Fluorescence intensity of the non-electroporated tumors treated with physiological saline or the different calcium chloride solutions rises over time. The fluorescence intensity of tumors treated with NaCl-EP decreases after treatment and thereafter increases.

Example 8

Hypothetical Example on Application of Sonoporation
Materials and Methods

Three cell lines are used for in vitro experiments, DC-3F, a transformed Chinese hamster lung fibroblast cell line; K-562, a human leukemia cell line; and Lewis Lung Carcinoma, a murine lung carcinoma cell line. All cell lines are tested for mycoplasma. Cells are maintained in RPMI 1640 culture medium with 10% fetal calf serum, penicillin and streptomycin at 37° C. and 5% CO2. After harvesting, cells are washed and diluted in HEPES buffer containing 10 mM HEPES, 250 mM sucrose and 1 mM $MgCl_2$ in sterile. The cell suspension with 0, 0.5, 1 and 3 mM $CaCl_2$ is added to a sample tube which is placed in the ultrasound exposure chamber and exposed to low-frequency ultrasound at room temperature. A function generator is programmed to provide a wave of selected voltage, duty cycle, burst length, and total exposure time.

After 20 min at 37° C. and 5% $CO_2$ cells are diluted in RPMI 1640 culture medium with 10% fetal calf serum and penicillin-streptomycin and seeded in 96-well plates at a concentration of $3.1 \times 10^4$ cells/100 μl. After respectively 1 and 2 days incubation MTT assay is performed using a MULTISKAN® ASCENT® ELISA reader (Thermo Labsystems, Philadelphia, Pa.).

Difference between cells treated with and without ultrasound in identical buffer is assessed using two-way analysis of variance CANOVA) with post least-squares-means test with Bonferroni correction for multiple comparisons.

Results

To test the effect of calcium overloading in vitro using ultrasound we use three cell lines from different species and of different tissue origin (DC-3F, a transformed Chinese hamster lung fibroblast cell line; K-562, a human leukemia cell line; Lewis Lung Carcinoma, a murine lung carcinoma cell line) in buffers containing increasing calcium concentrations (0 to 3 mM). Cell viability is determined respectively 1 and 2 days after treatment. This shows that ultrasound of cells in buffer containing calcium, induced dose dependent cell death in all three cell lines. In contrast, incubation at high calcium concentrations has no effect on cell viability in cells treated without ultrasound. There is a dramatic decrease in viability for all cell lines treated with ultrasound. The viability decrease significantly for all cell lines treated with ultrasound. As expected, due to differences in e.g. cell size and homogeneity there is a differential effect of the ultrasound procedure alone on the different cell lines. Consequently, values are listed as a percentage of controls treated with or without ultrasound, respectively. The decrease in viability after treatment with calcium and ultrasound is similar to the effect induced by calcium electroporation.

Example 9

Hypothetical Example on Application of Electromagnetic Field
Materials and Methods Three cell lines are used for in vitro experiments, DC-3F, a transformed Chinese hamster lung fibroblast cell line; K-562, a human leukemia cell line; and Lewis Lung Carcinoma, a murine lung carcinoma cell line. All cell lines are tested for mycoplasma. Cells are maintained in RPMI 1640 culture medium with 10% fetal calf serum, penicillin and streptomycin at 37° C. and 5% CO2. After harvesting, cells are washed and diluted in HEPES buffer containing 10 mM HEPES, 250 mM sucrose and 1 mM $MgCl^2$ in sterile water. The cell suspension with 0, 0.5, 1 and 3 mM $CaCl^2$ is transferred to the electroporation cuvette. A coil system is used to produce sufficiently strong electric fields by electromagnetic induction.

After 20 min at 37° C. and 5% $CO_2$ cells are diluted in RPMI 1640 culture medium with 10% fetal calf serum and penicillin-streptomycin and seeded in 96-well plates at a concentration of $3.1 \times 10^4$ cells/100 μl. After respectively 1 and 2 days incubation MTT assay is performed using a MULTISKAN® ASCENT® ELISA reader (Thermo Labsystems, Philadelphia, Pa.).

Difference between cells treated with or without electromagnetic field exposure in identical buffer is assessed using two-way analysis of variance (ANOVA) with post least-squares-means test with Bonferroni correction for multiple comparisons.

Results

To test the effect of calcium overloading in vitro using electromagnetic field exposure we use three cell lines from different species and of different tissue origin (DC-3F, a transformed Chinese hamster lung fibroblast cell line; K-562, a human leukemia cell line; Lewis Lung Carcinoma, a murine lung carcinoma cell line) in buffers containing increasing calcium concentrations (0 to 3 mM). Cell viability is determined respectively 1 and 2 days after treatment. This shows that electromagnetic field exposure of cells in buffer containing calcium, induced dose dependent cell death in all three cell lines. In contrast, incubation at high calcium concentrations has no effect on cell viability in cells treated without electromagnetic field exposure. There is a dramatic decrease in viability for all cell lines treated with electromagnetic. The viability decrease significantly for all cell lines treated with electromagnetic field. As expected, due to differences in e.g. cell size and homogeneity there is a differential effect of the electromagnetic field procedure alone on the different cell lines. Consequently, values are listed as a percentage of controls treated with or without electromagnetic field exposure, respectively. The decrease in viability after treatment with calcium and electromagnetic field exposure is similar to the effect induced by calcium electroporation.

Example 10

Hypothetical Example of Calcium Electroporation on Various Tumor Types
Materials and Methods In vivo experiments are performed in accordance with European Convention for the Protection of Vertebrate Animals used for Experimentation and with approval from the Danish Animal Experiments Inspectorate.

A squamous cell cancer of the head and neck cell line, a breast cancer cell line, a malignant melanoma cell linea colon cancer cell line and/or a sarcoma cell line is used for the in vivo experiments. The cells are tested by rapid MAP27 panel (Taconic, Hudson N.Y.) before use. Cells in 100l-11 PBS are injected subcutaneously in the flank of NMRI-Foxn1$^{nu}$ mice (Harlan, Indianapolis, Ind.) that are 9-11 weeks old. Mice are randomised at an average tumor size of 6 mm in largest diameter and tumors are treated with 1) injection of isotonic calcium-chloride solution (168 mM $CaCl^2$) and electroporation (8 pulses of 1.0 kV/cm for 100 μs and a frequency of 1 Hz) using a 6 mm plate electrode and a square wave electroporator (CLINIPORATOR®, IGEA, Modena, Italy), 2) calcium-free physiological saline injection and electroporation (same parameters as above), 3)

injection of isotonic calcium-chloride, or 4) calcium-free physiological saline injection. Tumor volume is calculated as $ab^2n/6$, where "a" is the largest diameter and "b" is the largest diameter perpendicular to "a". The injected volume is half of the tumor volume for all the groups. The solutions are injected through the side of the tumor and the needle is moved around inside the tumor to secure injection all over the tumor. Tumor size measurements using a Vernier caliper is performed before treatment and regularly after treatment.

The differences in tumor volume between tumors in the 4 treatment groups are evaluated as repeated measurements, validated and analysed with an exponential decrease model with Bonferroni correction for multiple comparisons using SAS® software version 9.1 (SAS, Cary, N.C.). 'Group', 'days' and 'mouse' are considered as factors and baseline levels of tumor volume are used as covariant.

Results $Ca^{2+}$-EP treatment eliminates 89% (8/9) of the treated tumors independently of tumor origin. Ulceration occurs in most of $Ca^{2+}$-EP treated tumors, with healing at an average of 18 days (range 9-24 days). Volume of tumors treated with $Ca^{2+}$-EP is significantly different from control tumors treated without electroporation ($p<0.0001$) as well as from tumors treated with NaCl-EP ($p<0.01$). Tumor volume of all non-electroporated tumors continues to increase with a doubling time of respectively 3.9 days (NaCl) and 6.3 days ($Ca^{2+}$). Tumors treated with NaCl-EP decrease in size in the first days after treatment but tumors start increasing in size. This indicates that electroporation alone can modulate tumor growth.

Example 11

Cell Death in Various Tumors
Materials and Methods

In vivo experiments were performed in accordance with European Convention for the Protection of Vertebrate Animals used for Experimentation and with approval from the Danish Animal Experiments Inspectorate.

LPB, a murine sarcoma cell line, B16, a murine malignant melanoma cell line, MDA-MB231, human a breast cancer cell line, HT29, a human colon cancer cell line, and SW780, a human bladder cancer cell line were used for the in vivo experiment. The cells were tested by rapid MAP27 panel (Taconic, Hudson N.Y.) before use without signs of infection. $2\times10^5$ cells (B16), $8\times10^5$ cells (LPB), $2.5\times10^6$ cells (MDA-MB231), and $5\times10^6$ cells (HT29 and SW780) in 100 µl PBS were injected subcutaneously in the flank of NMRI-Foxn1$^{nu}$ mice (Harlan, Indianapolis, Ind.) that were 9-11 weeks old. Mice were randomised at a tumor volume above 85 mm$^3$ and tumors were treated with injection of isotonic calcium-chloride solution (168 mM CaCl2) and electroporation (8 pulses of 1.0 kv/cm for 100 µs and a frequency of 1 Hz) using a 6 mm plate electrode and a square wave electroporator (CLINIPORATOR®, IGEA, Modena, Italy). Tumor volume was calculated as $ab^2n/6$, where a is the largest diameter and b is the largest diameter perpendicular to a. The injected volume was half of the tumor volume. The solution was injected through the side of the tumor and the needle was moved around inside the tumor to secure injection all over the tumor. Tumors were removed at skin level before treatment, 2 hours, 1, 2 and 6 days after treatment, fixated in formalin (10% neutrally buffered) and paraffin embedded. Subsequently, tissue sections with a thickness of 3 µm were HE-stained according to the routine procedure of the department. The fraction of necrosis within the tumor was estimated from HE-sections by stereological point counting using a light microscope, evaluated by a pathologist, blinded with respect to treatment status.

The difference in fraction of necrosis at different time after treatment was assessed using student's t-test.

Results

Figure 10:
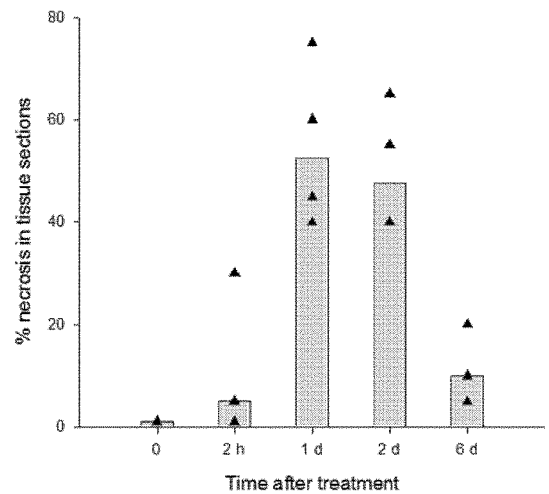
Figure 10:
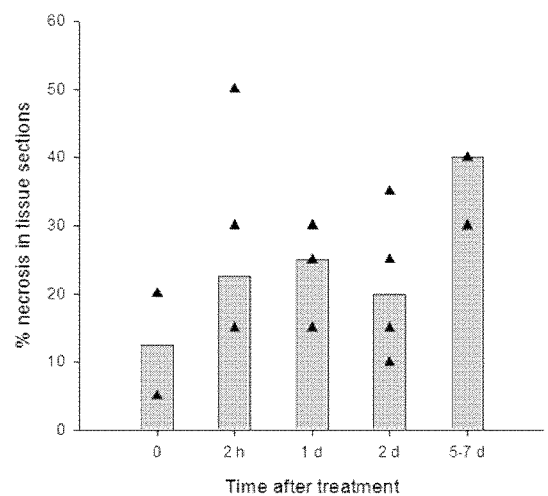
Figure 11:
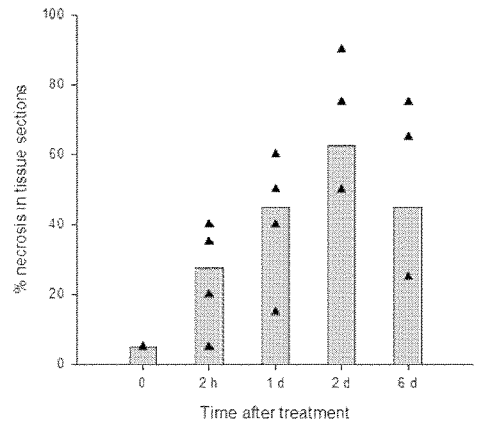
Figure 11:
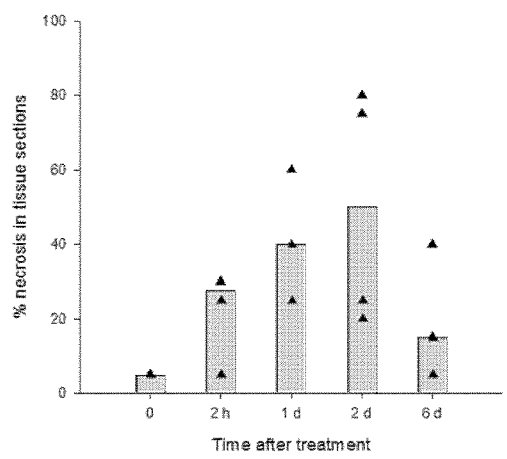
Figure 11:
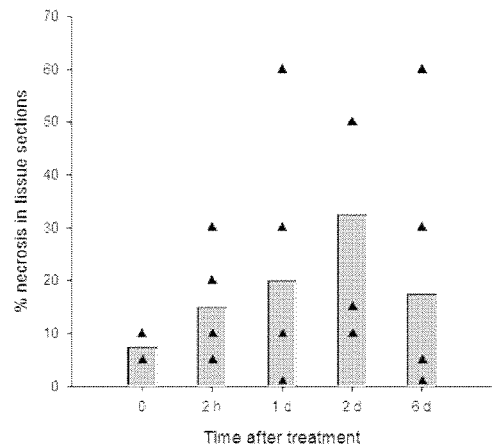

Histological analysis was performed on tissue sections of formalin-fixed, paraffin-embedded tumors treated with calcium electroporation. Sections were stained with hematoxylin/eosin (HE) and the fraction of necrosis was estimated. The analysis of calcium electroporation treated tumors shows progressive necrosis in all 5 different tumor types (FIGS. 10-11) the first days after the treatment which is significant in four of the tumor types ($p<0.05$ for MDA-MB231 at day 2, $p<0.05$ for HT29 and LPB at day 1, $p<0.01$ for LPB at day 2, $p<0.05$ for B16 at day 5-7). In four of the tumor types (LPB, MDA-MB231, HT29, and SW780) re-growth is seen 6 days after the treatment resulting in reduced fraction of necrosis. This could be due to untreated areas of the tumors or too low concentration and/or injection volume of calcium-chloride.

Conclusion

Calcium electroporation induce tumor necrosis in all five treated tumor types which is significant in four of the treated tumor types. Re-growth is seen in four of the tumor types which likely could be avoided by increasing the calcium concentration and/or the injected calcium volume or by re-treating the tumors.

Example 12

Application of Sonoporation
Materials and Methods

All in vivo experiments were approved by the ethics committee of University College Cork and carried out under license (Dr. Patrick Forde B100/4038) issued by the Department of Health, Ireland as directed by the Cruelty to Animals Act Ireland and EU Statutory Instructions.

CT26, a murine colon carcinoma cell line was used for the in vivo experiments. The cells were tested by mycoplasma detection kit (Sigma, St. Louis, Mo.) before use without signs of infection. Cells were maintained in vitro in DMEM culture medium (Sigma, St. Louis, Mo.) with 10% fetal calf serum (Sigma, St. Louis, Mo.), L-glutamine, penicillin and streptomycin at 37° C. and 5% $CO_2$. All antibiotics were removed from culture media 24 hours before tumour inoculation. $1.0\times10^6$ cells/200 µl serum free DMEM were injected subcutaneously in the right flank of 6-8 week old female Balb/c mice, in condition weighing 16-22 g. Mice were randomised at an average tumor size of approximately 5.0 mm in largest diameter and tumors were treated with 1) injection of isotonic calcium-chloride solution (168 mM $CaCl_2$) and sonoporation (3.5 W/cm$^2$ at 1 MHz and 100% duty cycle for 2 minutes) using a SONITRON® 2000 ultrasound apparatus (Rich-Mar, Inola, Okla.), 2) sonoporation alone (same parameters as above), 3) isotonic calcium-chloride solution injection, or 4) no treatment. Tumor volume was calculated as $ab^2n/6$, where a is the largest diameter and b is the largest diameter perpendicular to a. Tumors were injected with a volume of half the tumor volume and the solutions were injected through the side of the firm tumor and the needle was moved around inside the tumor to secure injection all over the tumor. Tumor size measurements using a Vernier caliper were performed before treatment and every second day after treatment.

The difference in tumor volume between the different treatment groups at different time after treatment was assessed using student's t-test.

Results

Figure 12:
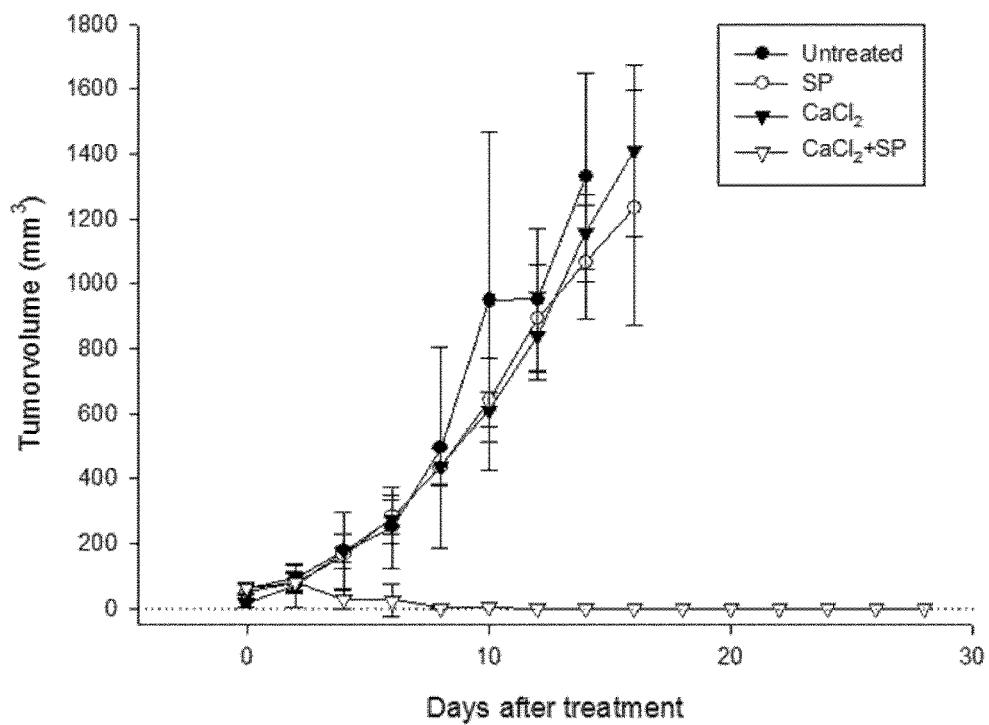

After showing a robust anti-cancer effect using electroporation in the presence of calcium, the effect of calcium in combination with sonoporation in vivo was tested. Murine colon carcinoma (CT26) tumors were treated with an isotonic calcium-chloride injection and sonoporated 'CaCl$_2$-SP') or in the case of controls, treated with sonoporation alone 'SP'), or isotonic calcium-chloride injection (CaCl$_2$), or untreated tumors (FIG. 12). Strikingly, CaCl$_2$-SP treatment eliminates 88% (7/8) of the treated tumors. Volume of tumors treated with CaCl$_2$-SP is significantly different from all three control groups (p<0.0001 at day 14 after treatment). Tumor volume of all control tumors continues to increase after the treatment.

Conclusion

Sonoporation induced loading of cancer cells with calcium is also a very efficient anti-cancer treatment.

Example 13

Calcium Electroporation with Two Different Calcium Sources
Materials and Methods DC-3F cells were electroporated as described in example 1 with 1 mM calcium chloride (prepared by SAD, Denmark) or 1 mM calcium glubionate (Sandoz, Holzkirchen, Germany). The calcium concentration was chosen based on the experiment described in example 1 where 1 mM calcium is the lowest concentration inducing high cell death. The cells were electroporated with 8 pulses of 991-1s at 1 Hz and increasing electric field (0-1.6 kV/cm). After 20 min at 37° C. and 5% CO$_2$ cells were diluted in RPMI 1640 culture medium with 10% fetal calf serum and penicillin-streptomycin and seeded in 96-well plates at a concentration of 3.1×10$^4$ cells/100 μl. The viability was measured 1 day after incubation by MTT assay using a MULTISKAN® ASCENT® ELISA reader (Thermo Labsystems, Philadelphia, Pa.).

The calcium concentration used in vitro is much lower than the calcium concentration used in vivo since the cells treated with calcium electroporation in vitro are in suspension and completely surrounded by the calcium solution whereas cells in a tumor treated with calcium electroporation are close together and the calcium solution is diluted when injected into the tumor.

Results

Figure 13:
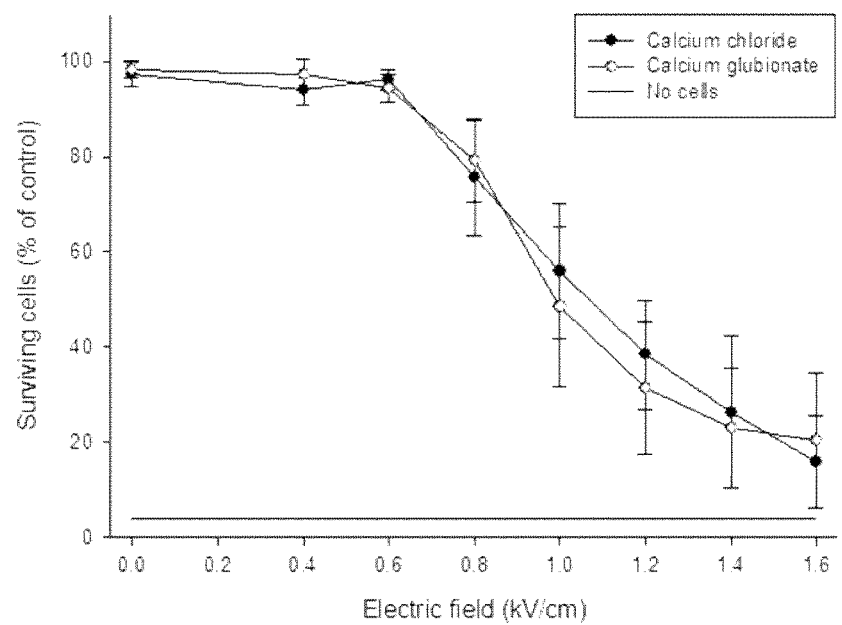

We have tested if there was any difference in the effect of calcium electroporation using calcium chloride or calcium glubionate. As seen in FIG. 13 there is no difference in the effect of calcium electroporation using the same concentration of calcium chloride or calcium glubionate.

Conclusion

There is no difference in the effect of calcium electroporation using different calcium sources at the same concentration.

Example 14

Effect of Electroporation with Calcium and/or Bleomycin
Materials and Methods

DC-3F, K-562 and Lewis Lung carcinoma cell lines were used for the in vitro experiment. The cell lines were maintained and harvested as described in example 1. Cells were electroporated (8 pulses of 991-1s, 1.2-1.4 kV/cm and 1 Hz) in HEPES buffer (as described in example 1) containing 0.01 μm bleomycin and/or 0.25 mM calcium chloride. The low concentration of bleomycin and calcium was chosen to be able to see an additive effect of the drugs. For in in vivo assays the concentration of calcium may be raised according to the present invention. After 2 days incubation MTT assay was performed using a MULTISKAN® ASCENT® ELISA reader (Thermo Labsystems, Philadelphia, Pa.).

Results

Figure 14:
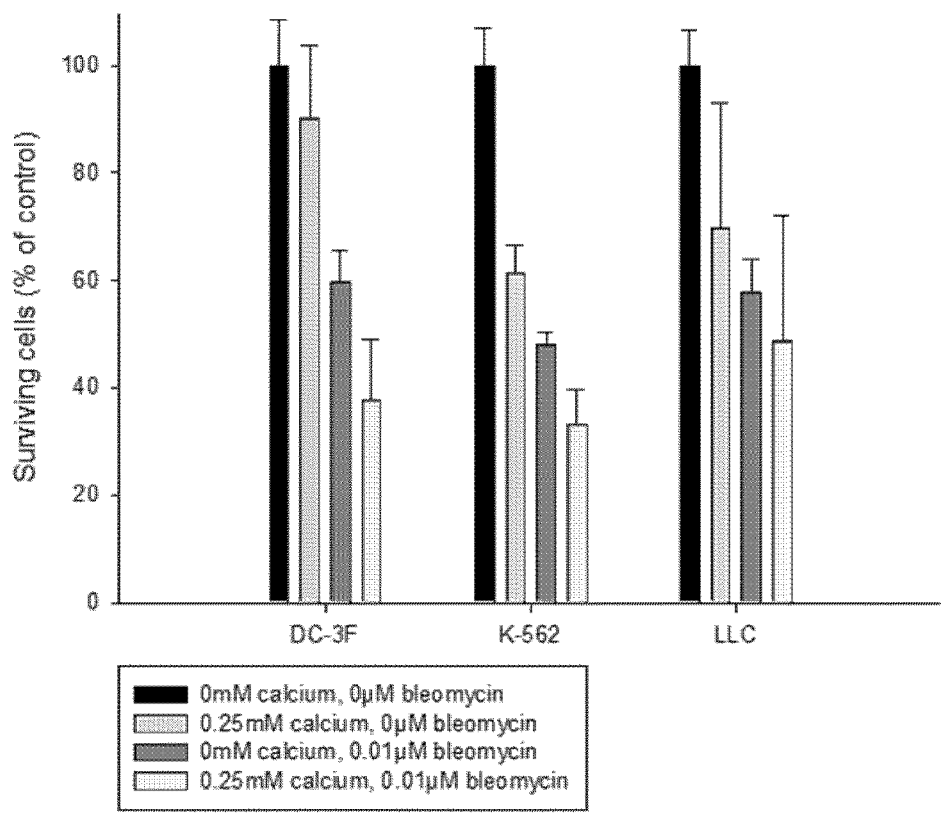

The effect of treatment with bleomycin, calcium, and electroporation was studied (FIG. 14) to test the effect of calcium and bleomycin together. The results indicate that there is an additive effect of calcium and bleomycin in all three tested cell lines.

Conclusions

Calcium and bleomycin in combination could be used clinically and there seems to be an additive effect of the two drugs. Such an additive effect may also be seen with calcium and another drug.

Example 15

Case Study—Calcium Electroporation of Canine Tumor
Materials and Methods

A seven year old Danish Pointer dog with a tumor on the heel joint was treated with calcium electroporation. The tumor was injected with 168 mM calcium chloride solution in a total volume equivalent to 50% of the tumor volume calculated as ab$^2$n/6, where "a" is the largest diameter of the tumor and "b" is the largest diameter perpendicular to "a". The calcium chloride solution was injected throughout the tumor to secure an even distribution of calcium in the tumor. After the calcium injection the tumor was electroporated (8 pulses of i oous at 1.0 kV/cm and 1 Hz) using a needle electrode and a square wave electroporator (CLINIPORATOR®, IGEA, Modena, Italy). The tumor was photographed before and after the treatment.

Results

Figure 15:
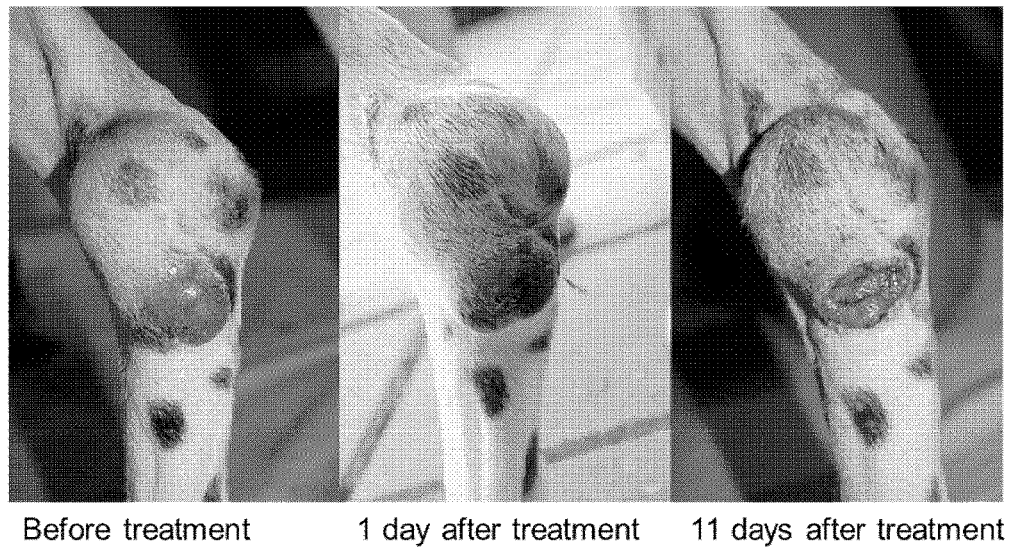

The photos of the tumor on the heel joint (FIG. 15) show the tumor before treatment and 1 day and 11 days after the treatment. The photos show that the tumor is reduced in size 11 days after treatment with calcium electroporation and the tumor is seen with clinical signs of necrosis.

Conclusion

Calcium electroporation can induce necrosis in a canine tumor.

Example 16

Calcium Electroporation of Brain Tumor
Materials and Methods

In vivo experiments were performed in accordance with European Convention for the Protection of Vertebrate Animals used for Experimentation and with approval from the Danish Animal Experiments Inspectorate.

N32, a rat brain glioma derived tumor cell line, and 7-11 weeks old Sprague Dawley male rats (Taconic, Hudson N.Y.) were used for the in vivo experiments. The cells were tested by rapid MAP27 panel (Taconic, Hudson N.Y.) before use without signs of infection. Inoculation of 3,000 N32 cells in 5 μl at the stereotaxic coordinates; X=2, Y=1, Z=−4 was performed and verification of tumor by MRI prior to treatment was performed two weeks after inoculation. HYPNORM™-DORMICUM™ (fentanyl/fluanisone/midazolam; VetaPharma, Leeds, U K and Roche, Basel, Switzerland) was used for anesthesia complemented with RIMADYL® (Carprofen) (Pfizer ApS, Ballerup, Denmark) for pain relief after surgery. Tumors were treated two weeks after inoculation with 1) injection of 14 μl calcium-chloride solution (168 mM) and electroporation (32 pulses of 100V for 100 µs and a frequency of 1 Hz) using an 8-electrode device developed for treatment of brain tumors, a square wave electroporator (CLINIPORATOR®, IGEA, Modena, Italy), and a switch box (Sonion), or 2) injection of 14 µl calcium-chloride solution (168 mM) and placement of electrodes but no pulses applied. MRI was performed at day 1, 3, 6, and 8 after treatment. After termination of the experiment the rat brains were prepared for immuno-histo-pathological staining by perfusing the rats with isotonic NaCl followed by 4% paraformaldehyde and kept at 5° C. for at least 24 hours. The extend of necrosis, the presence of macrophages and the influence on neurons and glia cells were evaluated by H&E, PAS, NF, and GFAP staining, respectively.

Results

Figure 16:
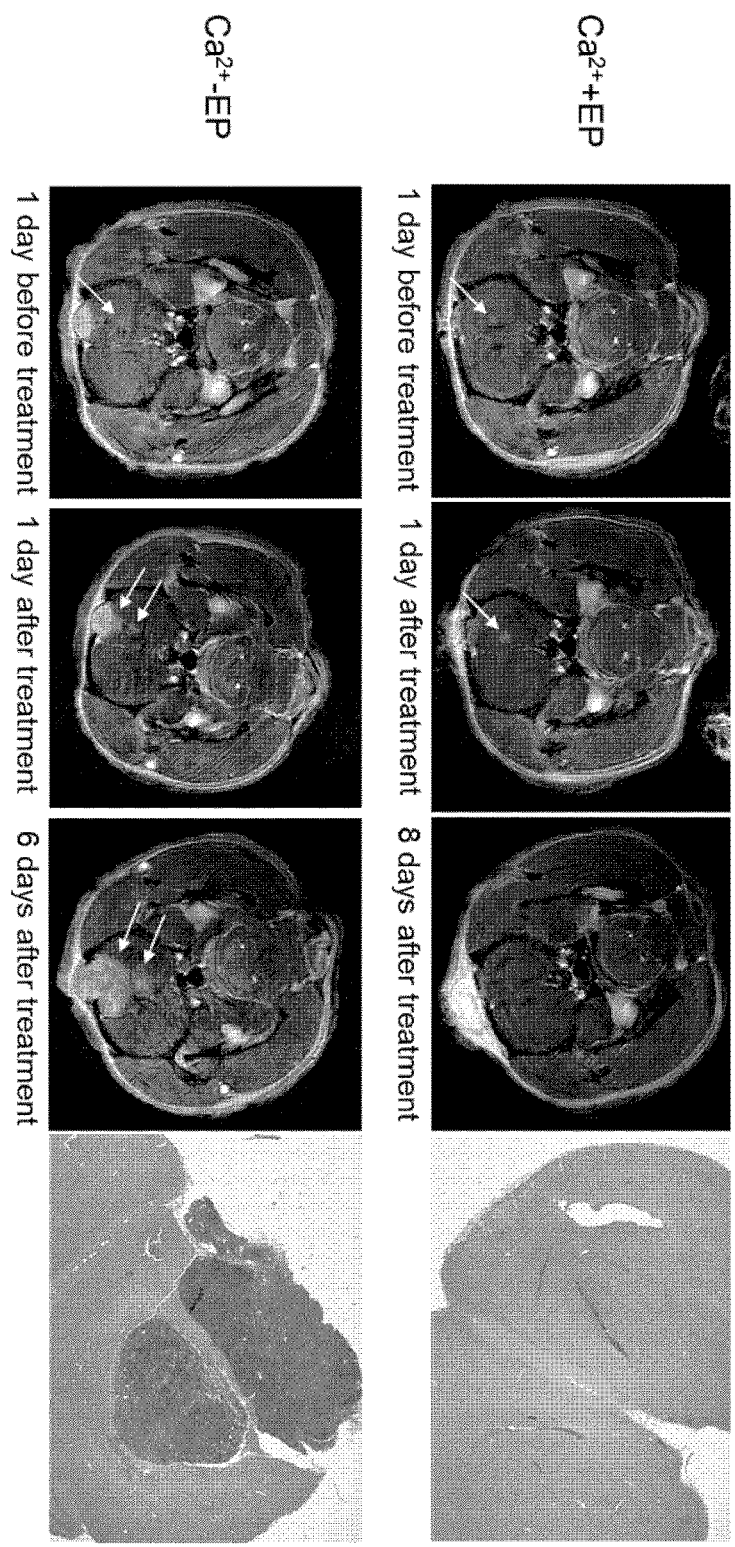

In FIG. 16 is shown MRI images of the tumor treated with calcium electroporation before treatment, 1 day and 8 days after treatment and the control tumor treated with calcium alone before treatment, 1 day and 6 days after treatment. Light microscope images of the H&E stained sections of the brain after termination of the experiment is also shown in the figure. The MRI images of the control tumor treated with calcium alone indicate that calcium alone has no effect on tumor size since the size of the tumor seems to increase 6 days after the treatment. The tumor is also clearly visible on the light microscope image of the H&E stained section of the tumor. The MRI images of the tumor treated with calcium electroporation indicate that the tumor is eliminated 8 days after the treatment which is also seen on the light microscope image of the H&E stained section of the brain where no tumor is seen.

Conclusion

Calcium electroporation is effective in a brain tumor.

Example 17

Normal Tissue Reaction

Materials and Methods

In vivo experiments were performed in accordance with European Convention for the Protection of Vertebrate Animals used for Experimentation and with approval from the Danish Animal Experiments Inspectorate.

MDA-MB231, a human breast cancer cell line was used for the in vivo experiments. The cells were tested by rapid MAP27 panel (Taconic, Hudson N.Y.) before use without signs of infection. Cells were maintained in vitro as described in Example 1. $2.5 \times 10^6$ cells/100 µl PBS were injected subcutaneously in the flank of NMRI-Foxn1nu mice (Harlan, Indianapolis, Ind.). Tumor pieces were transplanted twice from donor mice to the flank of nude mice that were 13-19 weeks old. HYPNORM™-DORMICUM™ (fentanyl/fluanisone/midazolam; VetaPharma, Leeds, U K and Roche, Basel, Switzerland) was used for anesthesia complemented with RIMADYL® (Carprofen) (Pfizer ApS, Ballerup, Denmark) as well as lidocaine (Region Hovedstadens Apotek, Herlev, Denmark) in the incision. Mice were randomised at a tumor volume above 85 mm³ and tumors were treated with 1) injection of calcium-chloride solution and electroporation (8 pulses of 1.0 kV/cm for 100 µs and a frequency of 1 Hz) using a 6 mm plate electrode and a square wave electroporator (CLINIPORATOR®, IGEA, Modena, Italy), 2) calcium-free physiological saline injection and electroporation (same parameters as above), 3) injection of calcium-chloride, 4) calcium-free physiological saline injection, or 5) untreated but with needle inserted in the tumor without injection and with electrodes put on the tumor without pulses applied. Three different concentrations of the calcium[ ]chloride solution were used: 100 mM, 220 mM and 500 mM and four different injection volumes of calcium chloride were used: 20%, 40%, 60% and 80% of the tumor volume. Tumor volume was calculated as ab2n/6, where "a" is the largest diameter and "b" is the largest diameter perpendicular to "a". The solutions were injected through the side of the firm tumor and the needle was moved around inside the tumor to secure injection all over the tumor. The skin above the tumor and the muscle beneath the tumor were removed 7 days after treatment, fixated in formalin (10% neutrally buffered) and paraffin embedded. Subsequently, tissue sections with a thickness of 31-1m were HE-stained according to the routine procedure of the department. Estimation of normal tissue damages was evaluated semiquantitatively on HE-sections by light[ ]microscopy (LEICA® DM 2000 light microscope, Leica Microsystems, Wetzlar, Germany).

The presence of inflammation in the skin dermis and subcutis was scored from 1-3 (1=minimal, 2=moderate and 3=severe). Edema in the dermis, extravasations of erythrocytes and vasculitis was noted if present, but not scored.

The presence of necrosis in the muscle samples were scored by counting numbers of necrotic myocytes per 10 HPF (400× magnification). Necrosis was only recorded if the myocytes had lost the nucleus. Increased eosinofilic intensity in the myocyte cytoplasm with a retained nucleus was not recorded as a necrotic fiber. Counting was performed in the area with the most obvious and worst morphological changes.

The results were grouped into 3 groups as follows:
no necrosis=0 necrotic myocytes/10HPF (0)
scattered, solitary necrotic myocytes or 1-4 necrotic myocytes/10HPF (1)
focal areas of coagulation necrosis or ≥5 necrotic myocytes/10HPF (2)

Interstitial inflammation, internalization of myocyte nuclei, extravasation of erythrocytes and vasculitis was noted if present, but not scored.

The skin biopsies and the muscle samples were not orientated, and hence location in relation to the electrodes not known.

Results

Figure 17:
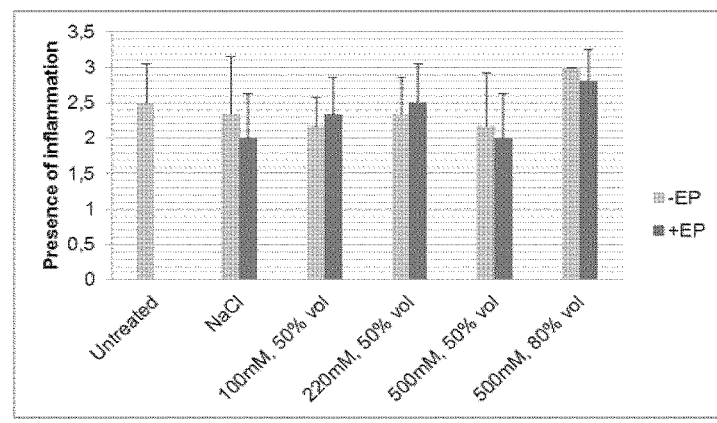
Figure 17:
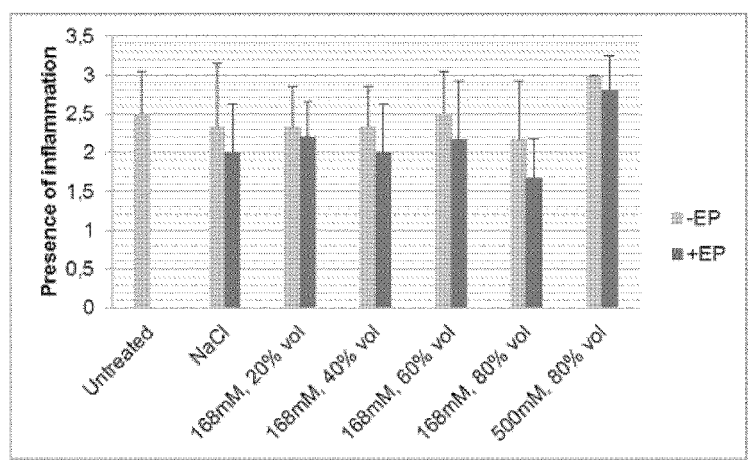

Inflammation in the skin located above the tumor after treatment was estimated (FIG. 17). The inflammation seen in the skin dermis and subcutis is dominated by mast cells and only few mononuclear cells and granulocytes are seen. In general, there is substantial degranulation of the mast cells, but in varying degree across samples. The epidermis is in general reactive with enlargement of the nuclei of the keratinocytes.

In subcutis, fat necrosis and reactive stromal changes could occasionally be observed, often present alongside severe inflammation in the dermis and subcutis and/or necrosis of muscle in the deep part of the biopsies.

As seen in FIG. 17 the presence of inflammation is similar in all the samples not depending on the treatment (untreated, physiological saline injection with or without electroporation, calcium injection with or without electroporation) nor depending on the concentration or injection volume of calcium showing that calcium electroporation is only affecting the surrounding normal skin tissue very little.

In some of the mice treated with the high concentration and volume of calcium ulceration above the tumor was seen but in previously experiments it has been shown that healing of the ulceration occurred in average 18 days (range, 9-24 days) after the treatment. Healing of the ulceration in this experiment was not seen since tumors were removed 7 days after the treatment.

The effect on the muscle tissue below the tumor was also examined. In general, all muscle tissue samples contains an increased number of mast cells lying in between the myocytes, and therefore none of the samples are considered completely normal. Mast cells are present in variable amounts, and with variable degrees of degranulation. In the majority of samples, the myocyte nuclei are enlarged and the chromatin structure reactively changed. A large number of samples show regeneration of myocytes with centrally located nuclei (internalization of nuclei). Focal areas of coagulation necrosis are only present in a minority of samples, but the majority samples show regenerative/reactive changes. In general, cross striation is retained. Extravasation of erythrocytes is only observed in a couple of samples.

Figure 18:
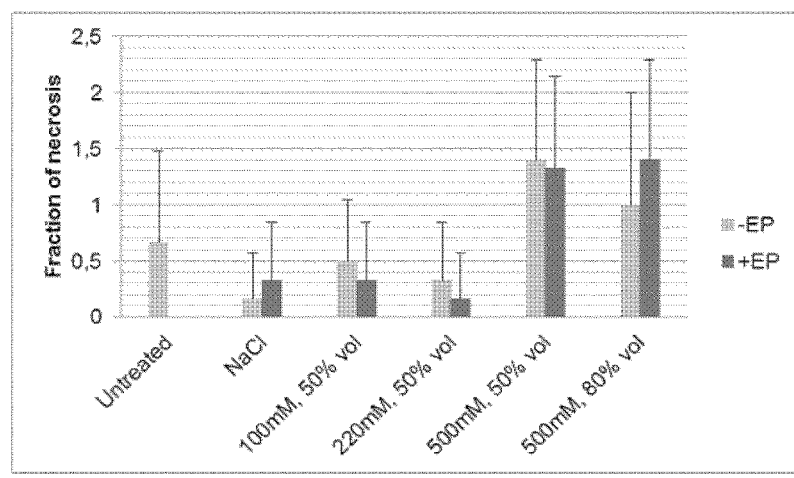
Figure 18:
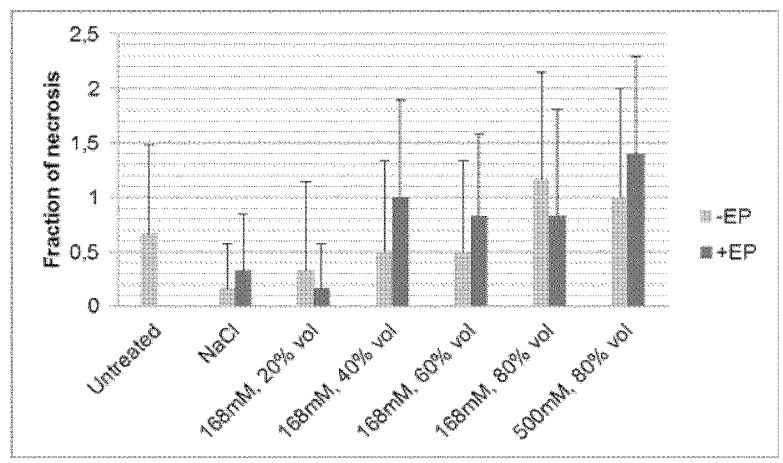

FIG. 18 shows the fraction of necrosis in the muscle tissue located below the treated tumor. The fraction of necrosis is grouped into three groups where 0 indicates no necrosis, 1 indicates scattered, solitary necrotic myocytes in the muscle tissue (maximum of 5% necrosis), and 2 indicates minor focal areas of coagulation necrosis (most of them below 10% necrosis and a few with 15-35% necrosis). As seen in the figure there is an increase in the fraction of necrosis at increasing calcium concentrations (FIG. 18) and also a slight increase in the fraction of necrosis at increasing injection volumes (FIG. 18). Even though the fraction of necrosis increases it is still only a minor fraction of the muscle tissue that is affected after calcium electroporation of the tumor above the muscle.

Conclusion

The anti-tumoral effects of calcium electroporation are limited to the relevant tumor cells, while sparing adjacent normal tissue. Skin tissue above the tumor is mildly affected following treatment, where inflammation is observed Inflammation may be attributed to needle insertion, as this was independent of treatment type. Muscle tissue below the treated tumor exhibits a small degree of necrosis, which increases slightly at higher calcium concentrations and injections volumes, yet remains low.

Example 18

Effect of Calcium Electroporation Using Different Calcium Concentrations and Injection Volumes Materials and Methods In vivo experiments were performed in accordance with European Convention for the Protection of Vertebrate Animals used for Experimentation and with approval from the Danish Animal Experiments Inspectorate.

MDA-MB231, a human breast cancer cell line was used for the in vivo experiments. The cells were tested by rapid MAP27 panel (Taconic, Hudson N.Y.) before use without signs of infection. Cells were maintained in vitro as described in Example 1. $2.5 \times 10^6$ cells/100 μl PBS were injected subcutaneously in the flank of NMRI-Foxn1nu mice (Harlan, Indianapolis, Ind.). Tumor pieces are transplanted twice from donor mice to the flank of nude mice that were 13-19 weeks old. HYPNORM™-DORMICUM™ (fentanyl/fluanisone/midazolam; VetaPharma, Leeds, U K and Roche, Basel, Switzerland) was used for anesthesia complemented with RIMADYL® (Carprofen) (Pfizer ApS, Ballerup, Denmark) as well as lidocaine (Region Hovedstadens Apotek, Herlev, Denmark) in the incision. Mice were randomised at a tumor volume above 85 mm3 and tumors were treated with 1) injection of calcium-chloride solution and electroporation (8 pulses of 1.0 kV/cm for 100 μs and a frequency of 1 Hz) using a 6 mm plate electrode and a square wave electroporator (CLINIPORATOR®, IGEA, Modena, Italy), 2) calcium-free physiological saline injection and electroporation (same parameters as above), 3) injection of calcium-chloride, 4) calcium-free physiological saline injection, or 5) untreated but with needle inserted in the tumor without injection and with electrodes put on the tumor without pulses applied. Three different concentrations of the calcium[ ]chloride solution were used: 100 mM, 220 mM, and 500 mM and four different injection volumes were used: 20%, 40%, 60%, and 80% of the tumor volume. Tumor volume was calculated as ab2n/6, where a is the largest diameter and b is the largest diameter perpendicular to a. The solutions were injected through the side of the firm tumor and the needle was moved around inside the tumor to secure injection all over the tumor. Tumors were removed 7 days after treatment, fixated in formalin (10% neutrally buffered) and paraffin embedded. Subsequently, tissue sections with a thickness of 3 μm were HE-stained according to the routine procedure of the department. The fraction of necrosis within the tumor was estimated from HE-sections using a light microscope, evaluated by a pathologist, blinded with respect to treatment status.

Results

The fraction of necrosis in tumors was estimated 7 days after treatment with calcium electroporation using different calcium concentrations (100 mM to 500 mM) and constant injection volume (50% of the tumor volume). This shows that the fraction of necrosis in these tumors is higher than the fraction of necrosis in untreated tumors.

Also in tumors treated with calcium electroporation using different injection volumes of calcium (20% to 80% of the tumor volume) and a constant calcium concentration (168 mM) the fraction of necrosis is higher than the fraction of necrosis in untreated tumors. The fraction of necrosis is highest in tumors treated with a volume of 40% of the tumor volume.

The effect of calcium electroporation using an injection volume of 80% of the tumor volume and a calcium concentration of 500 mM was estimated and in all five treated tumors there is between 80% and 100% necrosis.

Conclusions

The results of this experiment show that calcium electroporation using calcium concentrations between 100 mM and 500 mM and injection volumes between 20% and 80% of the tumor volume induces necrosis in the tumors. It is also seen that both calcium concentration and injection volume is affecting the fraction of necrosis induced by the treatment meaning that the calcium concentration and the injection volume have to be considered when planning the treatment. These results support the previous results showing that injecting volumes equal to the tumor volume leads to necrosis of surrounding healthy, whereas by lowering the volume this is avoided while still maintaining efficient treatment.

REFERENCES

Mashiba et al., [2005] Augmentation of antitumor and antimetastatic effect in combined use of electroporation with calcium chloride. Experimental and Molecular Therapeutics 17: Apoptosis: Therapeutic Applications, Abstract #2251

Mir, L. M. et al. Standard operating procedures of the electrochemotherapy: Instructions for the use of bleomycin or cisplatin administered either systemically or locally and electric pulses delivered by the Cliniporator™ by means of invasive or non-invasive electrodes. Eur J Cancer Suppl 4, 14-25 (2006).

The invention claimed is:

1. A method of treating a neoplasm in a subject comprising:
   a) administering to a subject having a neoplasm a solution comprising calcium ions ($Ca^{++}$) with a concentration of at least 0.1 M, wherein said solution is contacted with at least a part of said neoplasm, and wherein the volume of the solution has a ratio of 0.2 to 0.8 of the volume of said part of the neoplasm; and
   b) inducing transient permeabilisation of the cell membranes in said part of said neoplasm, wherein said transient permeabilisation commences before, during, or after said administration of said solution.

2. The method according to claim 1, wherein the calcium ions induce necrosis in at least 30% of the part of the neoplasm exposed to said transient permeabilisation of the cell membranes.

3. The method according to claim 1, wherein the transient permeabilisation of the cell membranes is induced by electroporation, sonoporation, a hydrodynamics-based procedure or a magnetic field.

4. The method according to claim 1, wherein the transient permeabilisation of the cell membranes is induced by an electroporation of 200-2000 V/cm; pulse length 0.1-10.0 ms; pulse number 2-20; and pulse frequency 1 Hz-5 kHz.

5. The method according to claim 1, wherein the transient permeabilisation is induced by sonoporation.

6. The method according to claim 1, wherein the subject is a mammal.

7. The method according to claim 1, wherein the neoplasm is a solid tumor.

8. The method according to claim 1, wherein the neoplasm is a solid tumor having a minimum diameter of 0.5 cm.

9. The method according to claim 1, wherein the solution is administrated by intratumoral injection or infusion.

10. The method according to claim 1, wherein the solution further comprises a chemotherapeutic agent or a cytotoxic agent.

11. The method according to claim 1, wherein the solution is free from a chemotherapeutic agent or a cytotoxic agent.

12. The method according to claim 1, wherein step a), alone step b) alone, or both of steps a) and b) are repeated one or more times.

* * * * *